United States Patent
Nirogi et al.

(10) Patent No.: US 12,156,871 B2
(45) Date of Patent: Dec. 3, 2024

(54) SUBSTITUTED AZACYCLES AS MUSCARINIC M1 RECEPTOR POSITIVE ALLOSTERIC MODULATORS

(71) Applicant: SUVEN LIFE SCIENCES LIMITED, Hyderabad-Telangana (IN)

(72) Inventors: Ramakrishna Nirogi, Hyderabad (IN); Anil Karbhari Shinde, Hyderabad (IN); Abdul Rasheed Mohammed, Hyderabad (IN); Rajesh Kumar Badange, Hyderabad (IN); Raghava Choudary Palacharla, Hyderabad (IN); Venkateswarlu Jasti, Hyderabad (IN)

(73) Assignee: SUVEN LIFE SCIENCES LIMITED, Hyderabad-Telangana (IN)

(*) Notice: Subject to any disclaimer, the term of this patent is extended or adjusted under 35 U.S.C. 154(b) by 383 days.

(21) Appl. No.: 16/766,112

(22) PCT Filed: Nov. 21, 2018

(86) PCT No.: PCT/IB2018/059164
§ 371 (c)(1),
(2) Date: May 21, 2020

(87) PCT Pub. No.: WO2019/102365
PCT Pub. Date: May 31, 2019

(65) Prior Publication Data
US 2021/0369685 A1 Dec. 2, 2021

(30) Foreign Application Priority Data
Nov. 23, 2017 (IN) .............................. 201741042082

(51) Int. Cl.
| | | |
|---|---|---|
| *A61P 25/28* | (2006.01) | |
| *A61K 31/13* | (2006.01) | |
| *A61K 31/27* | (2006.01) | |
| *A61K 31/437* | (2006.01) | |
| *A61K 31/4375* | (2006.01) | |
| *A61K 31/444* | (2006.01) | |
| *A61K 31/445* | (2006.01) | |
| *A61K 31/473* | (2006.01) | |
| *A61K 31/55* | (2006.01) | |
| *C07D 471/04* | (2006.01) | |

(52) U.S. Cl.
CPC ............ *A61K 31/437* (2013.01); *A61K 31/13* (2013.01); *A61K 31/27* (2013.01); *A61K 31/4375* (2013.01); *A61K 31/444* (2013.01); *A61K 31/445* (2013.01); *A61K 31/473* (2013.01); *A61K 31/55* (2013.01); *A61P 25/28* (2018.01); *C07D 471/04* (2013.01)

(58) Field of Classification Search
None
See application file for complete search history.

(56) References Cited

U.S. PATENT DOCUMENTS

2013/0109686 A1   5/2013  Beshore et al.

FOREIGN PATENT DOCUMENTS

| JP | 2017513894 A | 6/2017 |
|---|---|---|
| WO | 2012003147 A1 | 1/2012 |
| WO | 2012158475 A1 | 11/2012 |
| WO | 2013063549 A1 | 5/2013 |
| WO | 2015163485 A1 | 10/2015 |
| WO | 2018005249 A1 | 1/2018 |

OTHER PUBLICATIONS

Silverman RB. "The Organic Chemistry of Drug Design and Drug Action (Second Edition)". Section 2. Elsevier Academic Press. 2004, p. 29-32. (Year: 2004).*

Jennifer E. Davoren et al, "Design and Synthesis of [gamma]- and [delta]-Lactam M 1 Positive Allosteric Modulators (PAMs): Convulsion and Cholinergic Toxicity of an M 1 -Selective PAM with Weak Agonist Activity", Journal of Medicinal Chemistry, vol. 60, No. 15, Aug. 10, 2017 (Aug. 10, 2017), p. 6649-6663, XP055549757; DOI: 10.1021/acs.jmedchem.7b00597; ISSN:0022-2623.

(Continued)

*Primary Examiner* — Leslie A. Royds Draper
(74) *Attorney, Agent, or Firm* — IpHorgan Ltd.

(57) ABSTRACT

The present invention relates to compounds of formula (I), or their isotopic forms, stereoisomers, tautomers or pharmaceutically acceptable salt (s) thereof as muscarinic M1 receptor positive allosteric modulators (M1 PAMs). The present invention describes the methods of preparation, pharmaceutical composition, combinations and the use of compound formula (I), their stereoisomers, isotopic forms or pharmaceutically acceptable salts thereof.

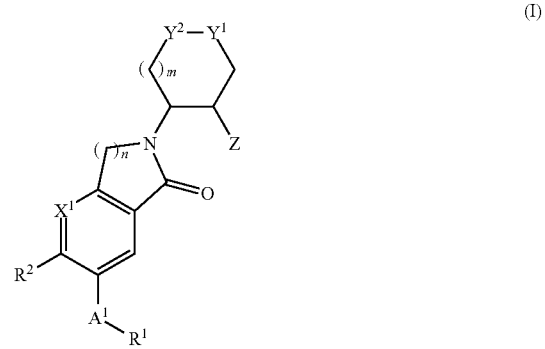

9 Claims, 1 Drawing Sheet

(56) References Cited

OTHER PUBLICATIONS

European Patent Office, Rijswijk, the Netherlands—PCT/IB2018/059164—International Search Report, Feb. 11, 2019.
European Patent Office, Munich, Germany—PCT/IB2018/059164—Written Opinion of the International Searching Authority, Feb. 11, 2019.
European Patent Office, Munich, Germany—PCT/IB2018/059164—International Preliminary Report on Patentability, Oct. 24, 2019.
Mistry, S. N. et al., ACS Chemical Neuroscience, 2016, Volo. 7, p. 647-661.
Scott D. Kuduk, Quinolizidinone Carboxylic Acids as CNS Penetrant, Selective M1 Allosteric Muscarinic Receptor Modulators, ACS Medicinal Chemistry Letters, 2010, 1, 263-267.
Scott D. Kuduk, Pyridine containing M1 positive allosteric modulators with reduced plasma protein binding, Bioorganic & Medicinal Chemistry Letters, 2010, 20, 657-661.

* cited by examiner

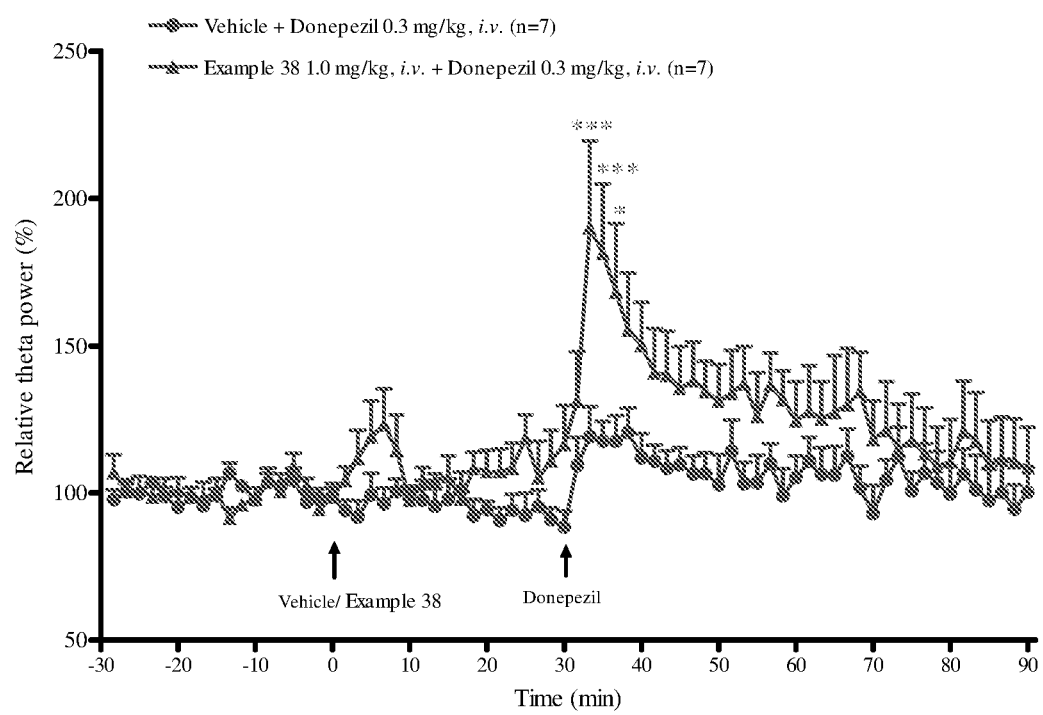
*$p<0.05$, ***$p<0.001$ Vs Donepezil alone (Bonferroni post test)

SUBSTITUTED AZACYCLES AS MUSCARINIC M1 RECEPTOR POSITIVE ALLOSTERIC MODULATORS

CROSS REFERENCE TO RELATED APPLICATIONS

This application is a national stage completion application of PCT Application No. PCT/IB2018/059164, filed Nov. 21, 2018, and claims priority from India Application No. 201741042082, filed Nov. 23, 2017. Each of these applications is incorporated by reference herein in its entirety.

FIELD OF INVENTION

The present invention relates to compounds of formula (I), or their isotopic forms, stereoisomers, or pharmaceutically acceptable salts as muscarinic M1 receptor positive allosteric modulators (M1 PAMs). The present invention also describes method of making such compounds, pharmaceutical compositions comprising such compounds, combinations and their use.

BACKGROUND OF THE INVENTION

Muscarinic acetylcholine receptors (mAChRs) which belong to the class A family of G protein-coupled receptors (GPCRs), are widely expressed throughout the body. Five subtypes termed M1 through M5 that respond to the endogenous neurotransmitter acetylcholine (ACh) has been identified till date. They play key role in regulating the activity of many important functions of the central and peripheral nervous system including cognitive function. M1, M3 and M5 couple to Gq, whereas M2 and M4 couple via Gi/o to downstream signaling pathways and associated effector systems (*Critical Reviews in Neurobiology*, 1996, 10, 69-99; *Pharmacology & Therapeutics*, 2008, 117, 232-243). M2 and M3 are highly expressed in the periphery and are known to be involved in gastrointestinal (GI) motility and parasympathetic responses such as salivation (*Life Sciences*, 1993, 52, 441-448). The M1 muscarinic receptor is predominantly expressed in the brain regions such as cortex, hippocampus and amygdala which involved in cognition, and therefore selective activation of the M1 receptor would be expected to boost cognitive performance (*Annals of Neurology*, 2003, 54, 144-146).

Xanomeline, a muscarinic acetylcholine receptor agonist with reasonable selectivity for the M1 and M4 subtypes, produced significant effects on cognition in a clinical Alzheimer's disease (AD) trial (*Alzheimer Disease and Associated Disorders*, 1998, 12(4), 304-312) although gastrointestinal side effects led to a high dropout rate in clinical trials. There is a high degree of conservation between muscarinic receptor subtypes at their orthosteric acetylcholine ligand binding sites which makes it difficult to identify a M1 selective agonist.

To circumvent this issue of selectivity and safety, an alternative approach consists of developing M1 PAMs that act at the less conserved allosteric binding site. Merck reported the development of M1 PAM, PQCA (1-{[4-cyano-4-(pyridine-2-yl)piperidin-1-yl] methyl}-4-oxo-4H-quinolizine-3-carboxylic acid). This compound is highly selective for M1 over the other muscarinic receptor subtypes and found to be efficacious in several preclinical models of cognition (*Psychopharmacology*, 2013, 225(1), 21-30) with no gastrointestinal side effects at doses equal to or less than a fivefold margin from the minimum effective dose required to improve cognition. In preclinical studies it was demonstrated that M1 activation increases neurotransmitter acetylcholine concentration in brain. Moreover, the M1 activation has potential as disease-modifying therapy for AD by both shifting the APP processing towards the non-amyloidogenic α-secretase pathway and by decreasing the tau hyper-phosphorylation. Positive allosteric modulators at M1 receptor have demonstrated to increase the generation of sAPPα in-vitro (*The Journal of Neuroscience*, 2009, 29, 14271-14286). Therefore, M1 PAMs provide an approach to target both symptomatic and disease-modifying treatment of cognitive deficits in AD and schizophrenia.

PCT patent application publications, WO2015163485, WO2012158475 and WO2012003147 have disclosed M1 PAM compounds. The articles, *J. Med. Chem.* 2017, 60, 6649-6663 and *J. Med. Chem.*, 2016, 59 (13), 6313-6328 also discloses M1 PAM compounds. While several M1 PAMs have been disclosed in the literature till date, no drug acting as M1 PAM is launched in the market.

Modern approaches for optimizing the ADME properties of compounds for CNS therapies incorporate compound's protein unbound fraction in plasma and brain as an important parameter. It is a commonly accepted hypothesis that availability of unbound or free drug concentration is important for interaction with pharmacological and toxicological targets in the brain. This hypothesis is referred to as the free drug hypothesis in pharmacokinetics (*Expert Opinion on Drug Discovery*, 2007, 2, 51-64; *Pharmaceutical Research*, 2008, 25, 1737-1750; *Current Drug Metabolism*, 2008, 9, 46-59; *Journal of Pharmaceutical Sciences*, 2010, 99, 1107-1122).

Although the prior arts disclose M1 PAM compounds that are useful in the treatment of CNS related diseases, there exist issues such as poor drug free fraction and cholinergic side effects like hypersalivation, diarrhea and emesis. Therefore, there is an unmet need and scope to discover and develop new M1 PAMs with adequate brain penetration with good drug free fraction, in addition to negligible cholinergic side effects in treatment of CNS related disorders. The M1 PAM compounds of the instant invention effectively addresses the issue of poor free fraction thereby enhances the probability of projecting the effective dose more accurately in humans.

SUMMARY OF THE INVENTION

In first aspect, the present invention relates to M1 PAMs of compound of formula (I),

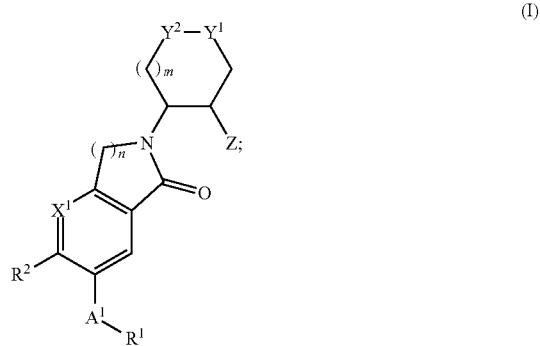

wherein:
R$^1$ is —(C$_{6-10}$-aryl, —(C$_{5-10}$)heteroaryl, or —(C$_{3-14}$)non-aromatic heterocyclyl; each of which is unsubstituted or substituted with one or more substituents selected from halogen, —OH, —O—(C$_{1-6}$)-alkyl, —S—(C$_{1-6}$)-alkyl, —N(CH$_3$)$_2$, —(C$_{1-6}$)-alkyl, —(C$_{3-6}$)-cycloalkyl, halo(C$_{1-6}$)-alkyl, —NH$_2$, —CN, —CONH$_2$, —CONH—(C$_{1-6}$)-alkyl and R$^{1a}$;
R$^{1a}$ is —(C$_{6-10}$)-aryl, —(C$_{5-10}$)-heteroaryl or —(C$_{3-14}$)-non-aromatic heterocyclyl; each of which is unsubstituted or substituted with one or more substituents selected from the group consisting of halogen, —OH, —NH$_2$, —CN, —O—(C$_{1-6}$)alkyl, —S—(C$_{1-6}$)-alkyl, —(C$_{1-6}$)-alkyl and —(C$_{3-6}$)-cycloalkyl;
A$^1$ is CH$_2$ or CHF;
R$^2$ is —(C$_{1-6}$)-alkyl;
X$^1$ is N or CR$^3$;
when X$^1$ is CR$^3$; then R$^3$ and R$^2$ combine together with the carbon atoms to which they are attached, form a non-aromatic 5- to 6-membered ring optionally containing one or more heteroatoms selected from nitrogen, oxygen and sulfur; wherein the said ring is unsubstituted or substituted with one or more groups selected from halogen, (C$_{1-6}$)-alkyl and halo(C$_{1-6}$)-alkyl;
n is 1 or 2; m is 0 or 1;
Y$^1$ is CH$_2$, O, NH or NCH$_3$;
Y$^2$ is CH$_2$, O, NH or NCH$_3$; and
Z is H, OH or F;
or an isotopic form, a stereoisomer, a tautomer or a pharmaceutically acceptable salt thereof.

In another aspect, the present invention relates to the processes for preparing the compound of formula (I), or a stereoisomer or a pharmaceutically acceptable salt thereof.

In yet another aspect, the present invention relates to pharmaceutical composition containing a therapeutically effective amount of at least one compound of formula (I), or a stereoisomer or a pharmaceutically acceptable salt thereof and pharmaceutically acceptable excipients or carriers.

In yet another aspect, the present invention relates to compound of formula (I), or a stereoisomer or a pharmaceutically acceptable salt thereof in combination with one or more other therapeutic agents selected from acetylcholinesterase inhibitors and NMDA receptor antagonist.

In yet another aspect, the present invention relates to compound of formula (I), or a stereoisomer or a pharmaceutically acceptable salt thereof, for use as muscarinic M1 receptor positive allosteric modulators.

In yet another aspect, the present invention relates to compound of formula (I), or a stereoisomer or a pharmaceutically acceptable salt thereof, for use in the treatment of disease or disorders selected from cognitive, pain or sleep disorders.

In yet another aspect, the present invention relates to compound of formula (I), or a stereoisomer or a pharmaceutically acceptable salt thereof, for use in the treatment of disease or disorders selected from Alzheimer's disease, schizophrenia, Parkinson's disease dementia, dementia due to Lewy body, pain or sleep disorder.

In another aspect, the present invention relates to a method for the treatment of disease or disorders related to muscarinic M1 receptor, comprising administering to a patient in need thereof, a therapeutically effective amount of a compound of formula (I), or a stereoisomer or a pharmaceutically acceptable salt thereof.

In yet another aspect, the present invention relates to use of the compound of formula (I), or a stereoisomer or a pharmaceutically acceptable salt thereof, for the manufacture of a medicament for the treatment of disease or disorders related to muscarinic M1 receptors.

In yet another aspect, the present invention relates to compound of formula (I) or a stereoisomer or a pharmaceutically acceptable salt thereof, for use in positive allosteric modulation of muscarinic M1 receptor.

BRIEF DESCRIPTION OF DRAWINGS

FIG. 1: Effect of test compound (Example 38) in combination with donepezil on hippocampal theta oscillations.

DETAILED DESCRIPTION OF THE INVENTION

Unless otherwise stated, the following terms used in the specification and claims have the meanings given below:

The term, "—(C$_{1-6}$)-alkyl" as used herein refers to branched or straight chain aliphatic hydrocarbon containing 1 to 6 carbon atoms. Examples of —(C$_{1-6}$)alkyl include methyl, ethyl, n-propyl, isopropyl, n-butyl, isobutyl, sec-butyl and tert-butyl. Preferably —(C$_{1-6}$)alkyl is methyl, ethyl or isopropyl.

The term, "halogen" or "halo" as used herein refers to fluorine, chlorine, bromine or iodine. Preferably, halogen is fluorine, chlorine or bromine. More preferably halogen is fluorine or chlorine.

The term "halo(C$_{1-6}$)alkyl" as used herein refers to (C$_{1-6}$)-alkyl as defined above wherein one or more hydrogen of the same or different carbon atom is substituted with same or different halogens. Examples of halo(C$_{1-6}$)alkyl include fluoromethyl, chloromethyl, fluoroethyl, difluoromethyl, dichloromethyl, trifluoromethyl, difluoroethyl and the like.

The term, "—(C$_{3-6}$)cycloalkyl" as used herein refers to saturated monocyclic hydrocarbon ring containing from three to six carbon atoms. Examples of —(C$_{3-6}$)-cycloalkyl group include cyclopropyl, cyclobutyl, cyclopentyl and cyclohexyl.

The term, "—(C$_{6-10}$)-aryl" as used herein refers to aromatic hydrocarbon rings containing six to ten carbon atoms. Examples of —(C$_{6-10}$)-aryl group include phenyl or naphthyl.

The term, —(C$_{5-10}$)heteroaryl as used herein refers to aromatic monocyclic or aromatic bicyclic heterocycle ring systems containing five to ten atoms. Examples of —(C$_{5-10}$)-heteroaryl group include 1,2,4-oxadiazolyl, 1,3,4-oxadiazolyl, 1,2,4-thiadiazolyl, 1,3,4-thiadiazolyl, triazolyl, tetrazolyl, triazinyl, furyl, imidazolyl, isoxazolyl, isothiazolyl, oxazolyl, pyrrolyl, pyrazolyl, thiazolyl, thienyl, pyridyl, pyrazinyl, pyrimidinyl, pyridazinyl, benzodioxolyl, benzofuranyl, benzofurazanyl, benzimidazolyl, benzopyrazolyl, benzothiazolyl, benzotriazolyl, benzothiophenyl, benzoxazepinyl, benzoxazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, isoquinolyl, quinolyl, phthalazinyl, naphthyridinyl, quinoxalinyl, quinazolinyl, and N-oxides thereof.

The term, "—(C$_{3-14}$)non-aromatic heterocyclyl" as used herein refers to non-aromatic monocyclic or non-aromatic bicyclic heterocycle ring systems containing three to fourteen atoms. Examples of —(C$_{3-14}$)non-aromatic heterocyclyl group includes but not limited to oxiranyl, aziridinyl, oxetanyl, piperidinyl, piperazinyl, dihydrobenzofuran, dihydrobenzothiophene, dihydroindole, tetrahydroquinoline and tetrahydroisoquinoline.

The phrase, "therapeutically effective amount" is defined as an amount of a compound of the present invention that (i) treats the particular disease, condition or disorder (ii) eliminates one or more symptoms of the particular disease, condition or disorder (iii) delays the onset of one or more symptoms of the particular disease, condition or disorder described herein.

The term, "isotopic form" as used herein refers to the compound of formula (I) wherein one or more atoms of compound of formula (I) are substituted by their respective isotopes. For example, isotopes of hydrogen include $^2H$ (deuterium) and $^3H$ (tritium).

The term, "stereoisomers" as used herein refers to isomers of compound of formula (I) that differ in the arrangement of their atoms in space. Compounds disclosed herein may exist as single stereoisomer, racemates and/or mixtures of enantiomers and/or diastereomers. All such single stereoisomer, racemates and mixtures thereof are intended to be within the scope of the present invention.

The term, "pharmaceutically acceptable salt" as used herein refers to salts of the active compound i.e. the compound of formula (I), and are prepared by reaction with the appropriate acid or acid derivative, depending on the particular substituents found on the compounds described herein.

The term, "cognitive disorder" as used herein refers to a group of mental health disorders that principally affect learning, memory, perception, and problem solving, and include amnesia, dementia, and delirium. Cognitive disorders can result due to disease, disorder, ailment or toxicity. Preferably the cognitive disorder is dementia. Example of dementia includes but not limited to, dementia in Alzheimer's disease, dementia in Parkinson's disease, dementia in Huntington's disease, dementia associated with Down syndrome, dementia associated with Tourette's syndrome, dementia associated with post menopause, frontotemporal dementia, Lewy body dementia, Vascular dementia, dementia in HIV, dementia in Creutzfeldt-Jakob disease, substance-induced persisting dementia, dementia in Pick's disease, dementia in schizophrenia, senile dementia and dementia in general medical conditions.

The term, "patient" as used herein refers to an animal. Preferably the term "patient" refers to mammal. The term mammal includes animals such as mice, rats, dogs, rabbits, pigs, monkeys, horses, pigeons, *Xenopus laevis*, zebrafish, guinea pigs and humans. More preferably the patient is human.

EMBODIMENTS

The present invention encompasses all the compounds described by the compound of formula (I) without any limitation, however, preferred aspects and elements of the invention are discussed herein in the form of the following embodiments.

In one embodiment, the present invention relates to the compound of formula (Ia), derived from compound of formula (I),

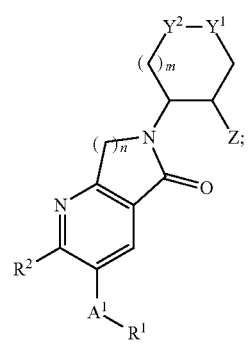

(Ia)

wherein:
$R^1$ is —$(C_{6-10})$-aryl, —$(C_{5-10})$-heteroaryl or —$(C_{3-14})$-non-aromatic heterocyclyl; each of which is unsubstituted or substituted with one or more substituents selected from halogen, —OH, —O—$(C_{1-6})$-alkyl, —S—$(C_{1-6})$-alkyl, —N(CH$_3$)$_2$, —$(C_{1-6})$-alkyl, —$(C_{3-6})$-cycloalkyl, halo$(C_{1-6})$-alkyl, —NH$_2$, —CN and $R^{1a}$;

$R^{1a}$ is —$(C_{6-10})$-aryl, —$(C_{5-10})$-heteroaryl or —$(C_{3-14})$-non-aromatic heterocyclyl; each of which is unsubstituted or substituted with one or more substituents selected from the group consisting of halogen, —OH, —NH$_2$, —CN, —O—$(C_{1-6})$-alkyl, —S—$(C_{1-6})$-alkyl, —$(C_{1-6})$-alkyl and —$(C_{3-6})$-cycloalkyl;

$A^1$ is CH$_2$ or CHF;
$R^2$ is —$(C_{1-6})$-alkyl;
n is 1 or 2; m is 0 or 1;
$Y^1$ is CH$_2$, O, NH or NCH$_3$;
$Y^2$ is CH$_2$, O, NH or NCH$_3$; and
Z is H, OH or F;
or an isotopic form, a stereoisomer, a tautomer or a pharmaceutically acceptable salt thereof.

In another embodiment, the present invention relates to the compound of formula (Ib), derived from compound of formula (I),

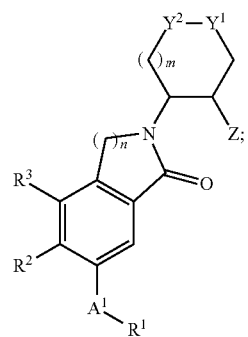

(Ib)

wherein:
$R^1$ is —$(C_{6-10})$-aryl, —$(C_{5-10})$-heteroaryl or —$(C_{3-14})$-non-aromatic heterocyclyl; each of which is unsubstituted or substituted with one or more substituents selected from halogen, —OH, —O—$(C_{1-6})$-alkyl, —S—$(C_{1-6})$-alkyl, —N(CH$_3$)$_2$, —$(C_{1-6})$-alkyl, —$(C_{3-6})$-cycloalkyl, halo$(C_{1-6})$-alkyl, —NH$_2$, —CN and $R^{1a}$;

$R^{1a}$ is —$(C_{6-10})$-aryl, —$(C_{5-10})$-heteroaryl or —$(C_{3-14})$-non-aromatic heterocyclyl; each of which is unsubstituted or substituted with one or more substituents selected from the group consisting of halogen, —OH, —NH$_2$, —CN, —O—(C$_{1-6}$)-alkyl, —S—(C$_{1-6}$)-alkyl, —(C$_{1-6}$)-alkyl and —(C$_{3-6}$)-cycloalkyl;

A$^1$ is CH$_2$ or CHF;

R$^3$ and R$^2$ combine together with the carbon atoms to which they are attached, form a non-aromatic 5- to 6-membered ring optionally containing one or more heteroatoms selected from nitrogen, oxygen and sulfur; wherein the said ring is unsubstituted or substituted with one or more groups selected from halogen, —(C$_{1-6}$)-alkyl and halo(C$_{1-6}$)-alkyl;

n is 1 or 2; m is 0 or 1:

Y$^1$ is CH$_2$, O, NH or NCH$_3$;

Y$^2$ is CH$_2$, O, NH or NCH$_3$; and

Z is H, OH, or F;

or an isotopic form, a stereoisomer, a tautomer or a pharmaceutically acceptable salt thereof.

In another embodiment, the present invention relates to the compound of formula (I), wherein: R$^1$ is —(C$_{6-10}$)-aryl, —(C$_{5-10}$)heteroaryl or —(C$_{3-14}$)-non-aromatic heterocyclyl; each of which is optionally substituted with one or more substituents selected from halogen, —OH, —O—(C$_{1-6}$)-alkyl, —S—(C$_{1-6}$)alkyl, —N—(CH$_3$)$_2$, —(C$_{1-6}$)alkyl, —(C$_{3-6}$)cycloalkyl, halo(C$_{1-6}$)-alkyl, —NH$_2$, —CN and R$^{1a}$; wherein R$^{1a}$ is as defined in the first aspect; or an isotopic form, a stereoisomer or a pharmaceutically acceptable salt thereof.

In another embodiment, the present invention relates to the compound of formula (I), wherein: R$^1$ is —(C$_{6-10}$)-aryl or —(C$_{5-10}$)-heteroaryl; each of which is optionally substituted with one or more substituents selected from halogen, —OH, —O—(C$_{1-6}$)-alkyl, —S—(C$_{1-6}$)-alkyl, —N(CH$_3$)$_2$, —(C$_{1-6}$)-alkyl, —(C$_{3-6}$)-cycloalkyl, halo(C$_{1-6}$)-alkyl, —NH$_2$, —CN and R$^{1a}$; wherein R$^{1a}$ is as defined in the first aspect; or an isotopic form, a stereoisomer or a pharmaceutically acceptable salt thereof.

In another embodiment, the present invention relates to the compound of formula (I), wherein: R$^1$ is —(C$_{6-10}$)-aryl which is optionally substituted with one or more substituents selected from halogen, —OH, O(C$_{1-6}$)alkyl, —S—(C$_{1-6}$) alkyl, —N(CH$_3$)$_2$, —(C$_{1-6}$)alkyl, —(C$_{3-6}$)cycloalkyl, halo (C$_{1-6}$)-alkyl, —NH$_2$, —CN and R$^{1a}$; wherein R$^{1a}$ is as defined in the first aspect; or an isotopic form, a stereoisomer or a pharmaceutically acceptable salt thereof.

In another embodiment, the present invention relates to the compound of formula (I), wherein: R$^1$ is —(C$_{5-10}$)-heteroaryl optionally substituted with one or more substituents selected from halogen, —OH, —O—(C$_{1-6}$)alkyl, —S—(C$_{1-6}$)-alkyl, —N(CH$_3$)$_2$, —(C$_{1-6}$)-alkyl, —(C$_{3-6}$)-cycloalkyl, halo(C$_{1-6}$)-alkyl, —NH$_2$, —CN and R$^{1a}$; wherein R$^{1a}$ is as defined in the first aspect; or an isotopic form, a stereoisomer or a pharmaceutically acceptable salt thereof.

In another embodiment, the present invention relates to the compound of formula (I), wherein: R$^1$ is —(C$_{3-14}$)-non-aromatic heterocyclyl optionally substituted with one or more substituents selected from halogen, —OH, —O—(C$_{1-6}$)alkyl, —S—(C$_{1-6}$)-alkyl, —N(CH$_3$)$_2$, —(C$_{1-6}$)-alkyl, —(C$_{3-6}$)-cycloalkyl, halo(C$_{1-6}$)-alkyl, —NH$_2$, —CN and R$^{1a}$; wherein R$^{1a}$ is as defined in the first aspect; or an isotopic form, a stereoisomer or a pharmaceutically acceptable salt thereof.

In another embodiment, the present invention relates to the compound of formula (I), wherein: R$^1$ is —(C$_{6-10}$)-aryl substituted with one or more R$^{1a}$; wherein R$^{1a}$ is as defined in the first aspect; or an isotopic form, a stereoisomer or a pharmaceutically acceptable salt thereof.

In another embodiment, the present invention relates to the compound of formula (I), wherein: R$^1$ is —(C$_{5-10}$)-heteroaryl substituted with one or more R$^{1a}$; wherein R$^{1a}$ is as defined in the first aspect; or an isotopic form, a stereoisomer or a pharmaceutically acceptable salt thereof.

In another embodiment, the present invention relates to the compound of formula (I), wherein: R1 is —(C3-14)non-aromatic heterocyclyl substituted with one or more R$^{1a}$; wherein R$^{1a}$ is as defined in the first aspect; or an isotopic form, a stereoisomer or a pharmaceutically acceptable salt thereof.

In yet another embodiment, the present invention relates to the compound of formula (I), wherein R$^3$ and R$^2$ taken together to form the rings selected from the group consisting of:

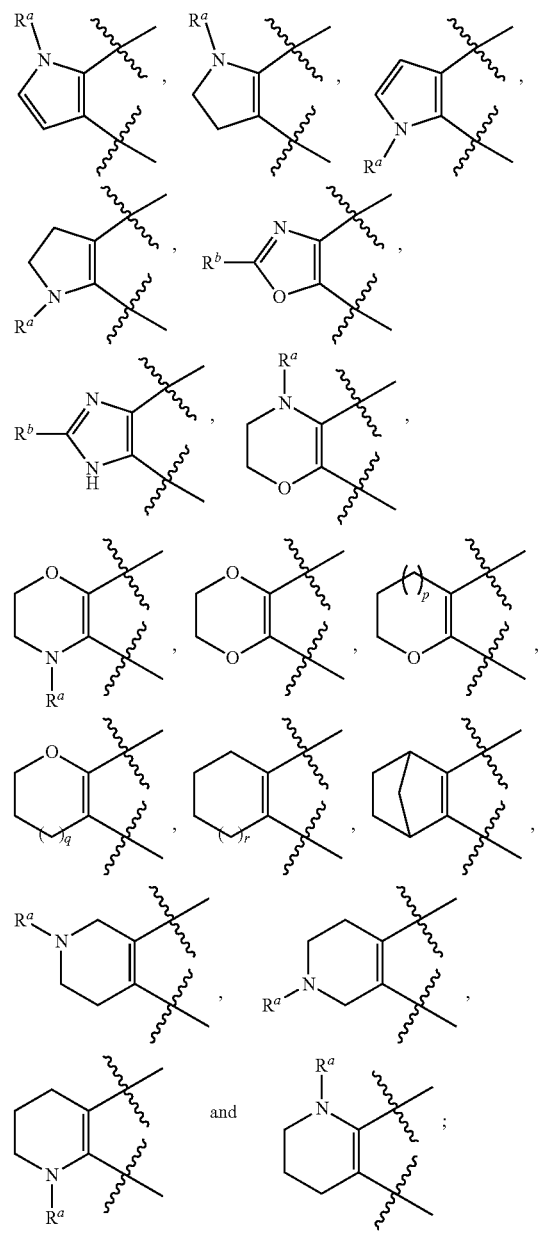

R$^a$ is hydrogen or —(C$_{1-6}$)-alkyl;
R$^b$ is hydrogen or —(C$_{1-6}$)-alkyl;

p is 0 or 1; q is 0 or 1; r is 0 or 1; or an isotopic form, a stereoisomer or a pharmaceutically acceptable salt thereof.

In yet another embodiment the representative compounds of the present invention includes but not limited to, 6-(1S,2S-2-Hydroxycyclohexyl)-2-methyl-3-(4-pyrazol-1-ylbenzyl)-6,7-dihydropyrrolo[3,4-b]pyridin-5-one;
6-(1S,2S-2-Hydroxycyclohexyl)-2-methyl-3-[2-(1-methyl-1H-pyrazol-4-yl)pyridin-5-ylmethyl]-6,7-dihydropyrrolo[3,4-b]pyridin-5-one;
6-(1S,2S-2-Hydroxycyclohexyl)-2-methyl-3-[4-(1-methyl-1H-pyrazol-4-yl)benzyl]-6,7-dihydropyrrolo[3,4-b]pyridin-5-one;
6-(1S,2S-2-Hydroxycyclohexyl)-2-methyl-3-(4-thiazol-4-ylbenzyl)-6,7-dihydropyrrolo[3,4-b]pyridin-5-one;
6-(1S,2S-2-Hydroxycyclohexyl)-2-methyl-3-(2,3-difluorobenzyl)-6,7-dihydropyrrolo[3,4-b]pyridin-5-one;
6-(1S,2S-2-Hydroxycyclohexyl)-2-methyl-3-(4-methoxybenzyl)-6,7-dihydropyrrolo[3,4-b]pyridin-5-one;
6-(1S,2S-2-Hydroxycyclohexyl)-2-methyl-3-(2-methylpyridin-5-ylmethyl)-6,7-dihydropyrrolo[3,4-b]pyridin-5-one;
6-(1S,2S-2-Hydroxycyclohexyl)-2-methyl-3-(2-fluoropyridin-4-ylmethyl)-6,7-dihydropyrrolo[3,4-b]pyridin-5-one;
6-(1S,2S-2-Hydroxycyclohexyl)-2-methyl-3-(4-fluorobenzyl)-6,7-dihydropyrrolo[3,4-b]pyridin-5-one;
6-(1S,2S-2-Hydroxycyclohexyl)-2-methyl-3-(3-fluorobenzyl)-6,7-dihydropyrrolo[3,4-b]pyridin-5-one;
6-(1S,2S-2-Hydroxycyclohexyl)-2-methyl-3-(2-fluoropyridin-5-ylmethyl)-6,7-dihydropyrrolo[3,4-b]pyridin-5-one;
6-(1S,2S-2-Hydroxycyclohexyl)-2-methyl-3-(2-chloropyridin-5-ylmethyl)-6,7-dihydropyrrolo[3,4-b]pyridin-5-one;
6-(4-Hydroxytetrahydropyran-3-yl)-3-(4-methoxybenzyl)-2-methyl-6,7-dihydropyrrolo[3,4-b]pyridin-5-one;
6-(1S,2S-2-Hydroxycyclohexyl)-2-methyl-3-(4-methoxybenzyl)-7,8-dihydro-6H-[1,6]naphthyridin-5-one;
6-(Tetrahydropyran-4-yl)-2-methyl-3-[2-(1-methyl-1H-pyrazol-4-yl)pyridin-5-ylmethyl]-6,7-dihydropyrrolo[3,4-b]pyridin-5-one;
6-(Tetrahydropyran-4-yl)-2-methyl-3-[4-(2-methyl-oxazol-4-yl)-benzyl]-6,7-dihydropyrrolo[3,4-b]pyridin-5-one;
6-(Tetrahydropyran-4-yl)-2-methyl-3-(4-thiazol-4-ylbenzyl)-6,7-dihydropyrrolo[3,4-b]pyridin-5-one;
6-(1S,2S-2-Hydroxycyclohexyl)-2-methyl-3-(3-chlorobenzyl)-7,8-dihydro-6H-[1,6]naphthyridin-5-one;
6-(1S,2S-2-Hydroxycyclohexyl)-2-methyl-3-(3,4-difluorobenzyl)-7,8-dihydro-6H-[1,6]naphthyridin-5-one;
6-(1S,2S-2-Hydroxycyclohexyl)-2-methyl-3-(2,3-difluorobenzyl)-7,8-dihydro-6H-[1,6]naphthyridin-5-one;
6-(1S,2S-2-Hydroxycyclohexyl)-2-methyl-3-(3-chlorobenzyl)-6,7-dihydropyrrolo[3,4-b]pyridin-5-one;
6-(1S,2S-2-Hydroxycyclohexyl)-2-methyl-3-[4-(2-methyl-oxazol-4-yl)-benzyl]-7,8-dihydro-6H-[1,6]naphthyridin-5-one;
6-(1S,2S-2-Hydroxycyclohexyl)-2-methyl-3-[4-chlorobenzyl]-7,8-dihydro-6H-[1,6]naphthyridin-5-one;
6-(1S,2S-2-Hydroxycyclohexyl)-2-methyl-3-(3-methoxybenzyl)-7,8-dihydro-6H-[1,6]naphthyridin-5-one;
6-(1S,2S-2-Hydroxycyclohexyl)-2-methyl-3-(6-methoxypyridin-3-ylmethyl)-6,7-dihydropyrrolo[3,4-b]pyridin-5-one;
6-(1S,2S-2-Hydroxycyclohexyl)-2-methyl-3-(4-chlorobenzyl)-6,7-dihydropyrrolo[3,4-b]pyridin-5-one;
6-(4-Hydroxy-tetrahydro-pyran-3-yl)-2-methyl-3-[4-methoxybenzyl]-7,8-dihydro-6H-[1,6]naphthyridin-5-one;
6-(1S,2S-2-Hydroxycyclohexyl)-2-methyl-3-(2-fluoropyridin-4-ylmethyl)-6,7-dihydropyrrolo[3,4-b]pyridin-5-one;
6-(1S,2S-2-Hydroxycyclohexyl)-2-methyl-3-(6-fluoropyridin-3-ylmethyl)-6,7-dihydropyrrolo[3,4-b]pyridin-5-one;
6-(1S,2S-2-Hydroxycyclohexyl)-2-methyl-3-(2-chloropyridin-4-ylmethyl)-6,7-dihydropyrrolo[3,4-b]pyridin-5-one;
6-(4-Hydroxytetrahydropyran-3-yl)-2-methyl-3-(4-pyrazol-1-yl-benzyl)-6,7-dihydro-pyrrolo[3,4-b]pyridin-5-one;
6-(4-Hydroxytetrahydropyran-3-yl)-2-methyl-3-[6-(1-methyl-1H-pyrazol-4-yl)-pyridin-3-ylmethyl]-6,7-dihydro-pyrrolo[3,4-b]pyridin-5-one;
6-(1S,2S-2-Hydroxycyclohexyl)-2-methyl-3-(4,4-difluoropiperidin-1-ylmethyl)-6,7-dihydropyrrolo[3,4-b]pyridin-5-one;
1-[6-(1S,2S-2-Hydroxycyclohexyl)-2-methyl-5-oxo-6,7-dihydro-5H-pyrrolo[3,4-b]pyridin-3-ylmethyl]-4-phenyl-piperidine-4-carbonitrile;
1-[6-(1S,2S-2-Hydroxycyclohexyl)-2-methyl-5-oxo-6,7-dihydro-5H-pyrrolo[3,4-b]pyridin-3-ylmethyl]-4-pyridyl-piperidine-4-carbonitrile;
1-[6-(1S,2S-2-Hydroxycyclohexyl)-2-methyl-5-oxo-5,6,7,8-tetrahydro-[1,6]naphthyridin-3-ylmethyl]-4-phenyl-piperidine-4-carbonitrile;
6-(3-Fluoro-piperidin-4-yl)-2-methyl-3-(4-methoxybenzyl)-6,7-dihydro-pyrrolo[3,4-b]pyridin-5-one;
6-(1S,2S-2-Hydroxycyclohexyl)-2-methyl-3-(3-methoxybenzyl)-6,7-dihydropyrrolo[3,4-b]pyridin-5-one;
6-(Tetrahydro-pyran-4-yl)-2-methyl-3-(4-methoxybenzyl)-6,7-dihydropyrrolo[3,4-b]pyridin-5-one;
6-(1S,2S-2-Hydroxycyclohexyl)-2-methyl-3-(3-fluorobenzyl)-7,8-dihydro-6H-[1,6]naphthyridin-5-one;
6-(Tetrahydro-pyran-4-yl)-2-methyl-3-(4-thiazol-4-yl-benzyl)-7,8-dihydro-6H-[1,6]naphthyridin-5-one;
6-(4-Hydroxy-tetrahydro-pyran-3-yl)-2-methyl-3-(4-pyrazol-1-yl-benzyl)-7,8-dihydro-6H-[1,6]naphthyridin-5-one;
6-(Tetrahydro-pyran-4-yl)-2-methyl-3-(3-methoxybenzyl)-6,7-dihydropyrrolo[3,4-b]pyridin-5-one;
6-(4-Hydroxy-tetrahydro-pyran-3-yl)-2-methyl-3-(4-methoxybenzyl)-6,7-dihydro-pyrrolo[3,4-b]pyridin-5-one-Cis-isomer (Ist Eluting isomer, Peak-I);
6-(4-Hydroxy-tetrahydro-pyran-3-yl)-2-methyl-3-(4-methoxybenzyl)-6,7-dihydro-pyrrolo[3,4-b]pyridin-5-one-Cis,Cis-isomer (IInd Eluting isomer, Peak-II);
6-(Tetrahydro-pyran-4-yl)-2-methyl-3-(4-methoxybenzyl)-7,8-dihydro-6H-[1,6]naphthyridin-5-one;
6-(Tetrahydro-pyran-4-yl)-2-methyl-3-(4-pyrazol-1-yl-benzyl)-6,7-dihydro-pyrrolo[3,4-b]pyridin-5-one;
6-(Tetrahydro-pyran-4-yl)-2-methyl-3-(4-pyrazol-1-yl-benzyl)-7,8-dihydro-6H-[1,6]naphthyridin-5-one;
6-(4-Hydroxy-tetrahydro-pyran-3-yl)-2-methyl-3-(4-fluorobenzyl)-7,8-dihydro-6H-[1,6]naphthyridin-5-one;
6-(4-Hydroxy-tetrahydro-pyran-3-yl)-2-methyl-3-(3-fluorobenzyl)-7,8-dihydro-6H-[1,6]naphthyridin-5-one; and
6-(4-Hydroxy-tetrahydro-pyran-3-yl)-2-methyl-3-(2,3-difluorobenzyl)-7,8-dihydro-6H-[1,6]naphthyridin-5-one;
or a pharmaceutically acceptable salt thereof.

In yet another embodiment the representative compounds of pharmaceutically acceptable salt of the present invention includes but not limited to, 1-[6-(1S,2S-2-Hydroxycyclohexyl)-2-methyl-5-oxo-6,7-dihydro-5H-pyrrolo[3,4-b]pyridin-3-ylmethyl]-4-pyridyl-piperidine-4-carbonitrile L-(+)-Tartrate;
1-[6-(1S,2S-2-Hydroxycyclohexyl)-2-methyl-5-oxo-5,6,7,8-tetrahydro-[1,6]naphthyridin-3-ylmethyl]-4-phenyl-piperidine-4-carbonitrile L-(+)-Tartrate; and 6-(3-Fluoro-piperidin-4-yl)-2-methyl-3-(4-methoxybenzyl)-6,7-dihydro-pyrrolo[3,4-b]pyridin-5-one hydrochloride;

Experimental Procedures

Scheme-1 depicts general processes for preparation of the compound of formula (I), wherein: T is —$(C_{1-6})$alkyl, $A^1$ is $CH_2$; $R^1$, $R^2$, $X^1$, $Y^1$, $Y^2$, n, m and Z are as defined above.

Step-1: Preparation of Compound of Formula 2

The compound of formula 2 is obtained by esterification of compound of formula 1 using alcohols under acidic conditions at a temperature in the range of −5° C. to 5° C. for 17 to 25 h.

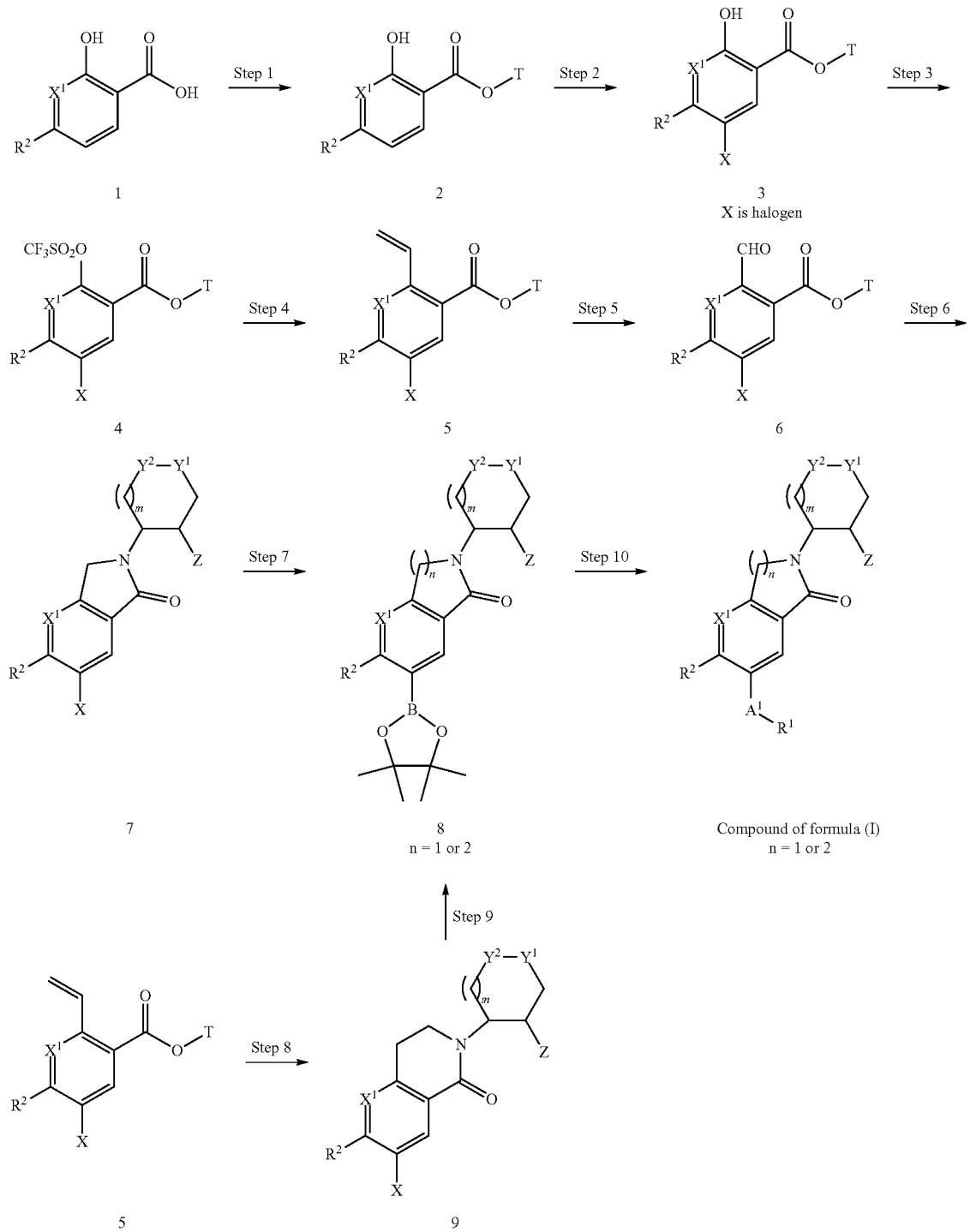

Scheme-1

Step-2: Preparation of Compound of Formula 3

The compound of formula 3 is obtained by reacting the compound of formula 2 with a halogenating agent selected from fluorine, chlorine, bromine under acidic conditions at room temperature for 1 to 3 h.

Step-3: Preparation of Compound of Formula 4

The compound of formula 4 is prepared by reacting the compound of formula 3 with N-phenylbis(trifluoromethanesulfonamide) in presence of base selected from sodium hydride, lithium hydride or potassium hydride and solvents selected from DMF or DCM at a room temperature for 15 to 20 h.

Step-4: Preparation of Compound of Formula 5

The compound of formula 5 is obtained by reacting the compound of formula 4 with tributylvinyltin, dichlorobis(triphenylphosphine) in presence of palladium chloride, lithium chloride and solvents such as DMF at the temperature in the range of 90° C. to 110° C. for 1 to 5 h under nitrogen atmosphere.

Step-5: Preparation of Compound of Formula 6

The compound of formula 6 is obtained by oxidizing the compound of formula 5 using oxidizing agents such as osmium oxide and sodium periodate in presence of solvent mixture selected from acetone, acetonitrile and water at room temperature for 1 to 5 h.

Step-6: Preparation of Compound of Formula 7

The compound of formula 7 is prepared by reacting the compound of formula 6 with amine,

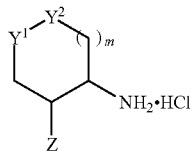

or its free base
in presence of coupling reagent, HATU, DCC, or EDC and a base, DIPEA in a solvent selected from DMF, THF, dichloromethane or 1,4-dioxane at room temperature for 35 to 50 h.

Step-7: Preparation of Compound of Formula 8

The compound of formula 8 is prepared by reacting compound 7 with bis(pinacolato)diboron in presence of dichloro[1,1'-bis(diphenylphosphino)ferrocene] palladium (II), complex, dichloromethane, potassium acetate and solvents such as 1,4-dioxane at the oil bath temperature for 1 to 5 h.

Step-8: Preparation of Compound of Formula 9

The compound of formula 9 is prepared by reacting the compound 5 with amine,

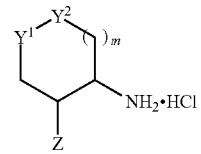

or its free base
in presence of alcoholic solvent like methanol at reflux temperature for 8 to 20 h.

Step-9: Preparation of Compound of Formula 8

The compound of formula 8 (n=1) is prepared similar to step-7 procedure.

Step-10: Preparation of Compound of Formula (I)

The compound of formula 8 is reacted with the compound of formula A, $$R^1-A^1-Cl \qquad A$$

in presence of [1,1'-bis(diphenylphosphino)ferrocene]palladium(II) dichloride and a base selected from potassium carbonate, cesium carbonate and sodium carbonate in a mixture of solvents such as water, THF and 1,4-dioxane under reflux for 3 to 7 h to obtain the compound of formula (I).

Preparation of Pharmaceutically Acceptable Salt of Compound of Formula (I)

The compound of formula (I) can optionally be converted into its pharmaceutically acceptable salt by reaction with the appropriate acid or acid derivative. Suitable pharmaceutically acceptable salts will be apparent to those skilled in the art. The salts are formed with inorganic acids e.g., hydrochloric, hydrobromic, sulfuric, nitric & phosphoric acid or organic acids e.g., oxalic, succinic, maleic, acetic, fumaric, citric, malic, tartaric, benzoic, p-toluic, p-toluenesulfonic, benzenesulfonic acid, methanesulfonic or naphthalenesulfonic acid.

Preparation of Stereoisomers of Compound of Formula (I)

The stereoisomers of compounds of formula (I) may be prepared by one or more conventional ways presented below:

a. One or more of the reagents may be used in their optically active form.

b. The mixture of stereoisomers may be resolved by conventional methods such as forming diastereomeric salts with chiral acids or chiral amines or chiral amino alcohols, or chiral amino acids. The resulting mixture of diastereomers may then be separated by methods such as fractional crystallization, chromatography and the like, which is followed by an additional step of isolating the optically active product from the resolved material/salt.

c. The mixture of stereoisomers may be resolved by conventional methods such as microbial resolution, resolving the diastereomeric salts formed with chiral acids or chiral bases. Chiral acids that can be employed may be tartaric acid, mandelic acid, lactic acid, camphorsulfonic acid, amino acids and the like. Chiral bases that can be employed may be cinchona alkaloids, brucine or a basic amino acid such as lysine, arginine and the like.

In another embodiment, the suitable pharmaceutically acceptable salt includes hydrochloride, hydrobromide, oxalate, fumarate, tartrate, maleate and succinate.

In another aspect of the present invention, the compound of formula (I) are muscarinic M1 positive alloseteric modulators.

In another aspect, the present invention relates to a method of treating the disease or disorder selected from cognitive disorder, schizophrenia, pain or sleep disorder, comprising administering to a patient in need thereof, a therapeutically effective amount of compounds of formula (I) or a pharmaceutically acceptable salt thereof.

In another aspect, the present invention relates to a method of treatment of Alzheimer's disease comprising administering to a patient in need thereof, a therapeutically effective amount of compounds of formula (I) or a pharmaceutically acceptable salt thereof.

In another aspect, the present invention relates to a method of treatment of Alzheimer's disease including mild Alzheimer's disease, moderate Alzheimer's disease, severe Alzheimer's disease, mild to moderate Alzheimer's disease or moderate to severe Alzheimer's disease, comprising administering to a patient in need thereof, a therapeutically effective amount of compounds of formula (I) or a pharmaceutically acceptable salt thereof.

In yet another aspect, the present invention relates to compound of formula (I) for use in the treatment of disease or disorder selected from cognitive disorder, pain or sleep disorder.

In yet another aspect, the present invention relates to use of the compound of formula (I) in the manufacture of medicament for the treatment of disease or disorder selected from cognitive disorder, pain or sleep disorder.

In yet another aspect, the present invention relates to use of the compound of formula (I) in the manufacture of medicament for the treatment of disease or disorder selected from cognitive disorder.

In yet another aspect, the present invention relates to use of the compound of formula (I) in the manufacture of medicament for the treatment of Alzheimer's disease.

In yet another embodiment, the present invention relates to the combination of compound of formula (I) with one or more other therapeutic agents such as acetylcholinesterase inhibitors and NMDA receptor antagonist.

In another embodiment, the compound of formula (I) of the present invention may be used in combination with one or more other therapeutic agents in the treatment of diseases or disorders for which the compound of formula (I) of the present invention have utility. Examples of the combinations of the compounds of present invention include combination with the therapeutic agents for the treatment of Alzheimer's disease, for example acetylcholinesterase inhibitors such as galantamine, rivastigmine, donepezil, and tacrine; and NMDA receptor antagonist such as memantine.

In yet another embodiment, the present invention relates to combination of compound of formula (I) with at least one therapeutic agents selected from galantamine, rivastigmine, donepezil, tacrine and memantine.

In yet another embodiment the present invention relates to the combination of compound of formula (I) with one or more other therapeutic agents such as acetylcholinesterase inhibitors and NMDA receptor antagonist for use in the treatment of cognitive disorder, schizophrenia, pain and sleep disorder.

In yet another embodiment the present invention relates to the combination of compound of formula (I) with one or more other therapeutic agents selected from acetylcholinesterase inhibitors and NMDA receptor antagonist for use in the treatment of Alzheimer's disease.

In yet another aspect, the present invention relates to the pharmaceutical composition of the compound of formula (I). In order to use the compound of formula (I), or their stereoisomers and pharmaceutically acceptable salts thereof in therapy, they will normally be formulated into a pharmaceutical composition in accordance with standard pharmaceutical practice.

The pharmaceutical compositions of the present invention may be formulated in a conventional manner using one or more pharmaceutically acceptable excipients. The pharmaceutically acceptable excipients are diluents, disintegrants, binders, lubricants, glidants, polymers, coating agents, solvents, cosolvents, preservatives, wetting agents, thickening agents, antifoaming agents, sweetening agents, flavouring agents, antioxidants, colorants, solubilizers, plasticizer, dispersing agents and the like. Excipients are selected from microcrystalline cellulose, mannitol, lactose, pregelatinized starch, sodium starch glycolate, corn starch or derivatives thereof, povidone, crospovidone, calcium stearate, glyceryl monostearate, glyceryl palmitostearate, talc, colloidal silicone dioxide, magnesium stearate, sodium lauryl sulfate, sodium stearyl fumarate, zinc stearate, stearic acid or hydrogenated vegetable oil, gum arabica, magnesia, glucose, fats, waxes, natural or hardened oils, water, physiological sodium chloride solution or alcohols, for example, ethanol, propanol or glycerol, sugar solutions, such as glucose solutions or mannitol solutions and the like or a mixture of the various excipients.

In yet another aspect, the active compounds of the invention may be formulated in the form of pills, tablets, coated tablets, capsules, powder, granules, pellets, patches, implants, films, liquids, semi-solids, gels, aerosols, emulsions, elixirs and the like. Such pharmaceutical compositions and processes for preparing same are well known in the art.

In yet another aspect, the pharmaceutical composition of the instant invention contains 1 to 90%, 5 to 75% and 10 to 60% by weight of the compounds of the instant invention or pharmaceutically acceptable salt thereof. The amount of the active compounds or its pharmaceutically acceptable salt in the pharmaceutical composition(s) can range from about 1 mg to about 500 mg or from about 5 mg to about 400 mg or from about 5 mg to about 250 mg or from about 7 mg to about 150 mg or in any range falling within the broader range of 1 mg to 500 mg.

The dose of the active compounds can vary depending on factors such as age and weight of patient, nature and severity of the disease to be treated and such other factors. Therefore, any reference regarding pharmacologically effective amount of the compounds of general formula (I), stereoisomers and pharmaceutically acceptable salts thereof refers to the aforementioned factors.

The following abbreviations are used herein:
AMP: Adenosine monophosphate
AUC: Area under the curve
$C_{max}$: Maximum concentration
DCM: Dichloromethane
DCC: N,N'-Dicyclohexylcarbodiimide
DIPEA: N,N-Diisopropylethylamine
DMF: N,N-Dimethylformamide
DMSO: Dimethyl sulfoxide
$EC_{50}$: Half maximal effective concentration EDC: Ethylene dichloride
Fu: Fraction of compound unbound to proteins
g: Gram (s)
h: Hour (s)
HATU: 2-(7-Aza-1H-benzotriazole-1-yl)-1,1,3,3-tetramethyluronium hexafluorophosphate
HCl: Hydrochloric acid
LC-MS/MS: Liquid chromatography-Mass spectrometry/Mass spectrometry
$Na_2SO_4$: Sodium sulphate
RT: Room temperature (25° C. to 30° C.)
ROA: Route of Administration
p.o: Per Oral
THF: Tetrahydrofuran
$T_{1/2}$: Half-life time

EXAMPLES

The compounds of the present invention were prepared according to the following experimental procedures, using appropriate materials and conditions. The following examples are provided by way of illustration only but not to limit the scope of present invention.

Preparation of Intermediates

Intermediate 1:
1-(4-Bromomethylphenyl)-1H-pyrazole (I-1)

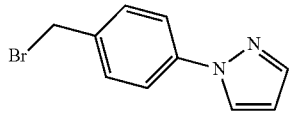 [SMILES: BrCc1ccc(-n2cccn2)cc1]

Step-1: To a solution of 4-bromobenzaldehyde (2.0 g, 0.010 mole) in DMF 20 mL under $N_2$ at 25° C., was added 1H-pyrazole (0.668 g, 0.0098 mole), copper iodide (0.185 g, 0.0009 mole), L-proline (0.224 g, 0.0019 mole) and cesium carbonate (6.4 g, 0.0196 mole). The reaction mixture was heated to 120° C. for 20 h, cooled to RT, filtered through celite and washed with ethyl acetate (50 mL). The filtrate was concentrated under vacuum to obtain the crude compound which was further purified by flash chromatography using ethyl acetate: n-hexane (20:80) to obtain 4-(pyrazol-1-yl)benzaldehyde.

Yield: 1.0 g; $^1$H-NMR (DMSO-$d_6$, 400 MHz) δ ppm: 6.62 (s, 1H), 7.84 (s, 1H), 8.01-8.03 (d, J=8.4 Hz, 2H), 8.07 (d, J=8.4 Hz, 2H), 8.67 (s, 1H), 10.00 (s, 1H); Mass (m/z): 173.1 (M+H)$^+$.

Step-2: To a cooled solution of 4-(pyrazol-1-yl)benzaldehyde (3.0 g, 0.017 mole) in methanol (20 mL) under $N_2$, was added sodium borohydride (0.79 g, 0.02 mole) in portion wise. The reaction mixture was warmed to RT and stirred for 2 h. The reaction mixture was concentrated under vacuum, dissolved in ice cold water (75 mL) and extracted with ethyl acetate (100 mL×2). Organic layer was washed with brine solution (50 mL), dried over $Na_2SO_4$ and concentrated under vacuum to obtain the crude compound which was further purified by flash chromatography using ethyl acetate: n-hexane (40:60) to get 1-(4-hydroxymethylphenyl)-1H-pyrazole.

Yield: 2.4 g; $^1$H-NMR (DMSO-$d_6$, 400 MHz) δ ppm: 4.52-4.53 (d, J=5.6 Hz, 2H), 5.23-5.26 (t, J=5.7 Hz, 1H), 6.52 (s, 1H), 7.41-7.43 (d, J=8.3 Hz, 2H), 7.72 (s, 1H), 7.77-7.79 (d, J=8.3 Hz, 2H), 8.09 (d, J=2.3 Hz, 1H); Mass (m/z): 175.1 (M+H)$^+$.

Step-3: To a solution of 1-(4-hydroxymethylphenyl)-1H-pyrazole (1.0 g, 0.005 mole) in DCM (25 mL) at 0° C. under $N_2$, was added phosphorus tribromide (0.64 mL, 0.0068 mole) drop wise. Reaction mixture was warmed to RT and stirred for 2 h. The reaction mixture was diluted with DCM (75 mL), treated with saturated aqueous sodium bicarbonate (20 mL). Organic layer was washed with water (30 mL), brine solution (30 mL) and dried over $Na_2SO_4$ and concentrated under vacuum to obtain the title compound.

Yield: 1.25 g; $^1$H-NMR (DMSO-$d_6$, 400 MHz) δ ppm: 4.76 (s, 2H), 6.55 (s, 1H), 7.56-7.58 (d, J=8.5 Hz, 2H), 7.75 (s, 1H), 7.82-7.84 (d, J=8.4 Hz, 2H), 8.51-8.52 (d, J=2.4 Hz, 1H); Mass (m/z): 236.9 (M+H)$^+$, 239 (M+H)$^±$.

Example 1

6-(1S,2S-2-Hydroxycyclohexyl)-2-methyl-3-(4-pyrazol-1-ylbenzyl)-6,7-dihydropyrrolo[3,4-b]pyridin-5-one

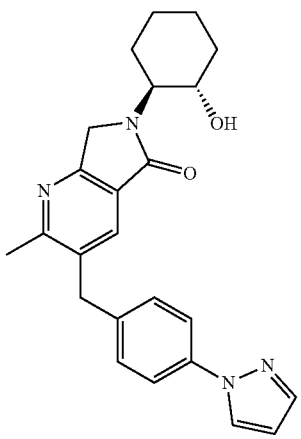 [SMILES: Cc1nc2c(cc1Cc1ccc(-n3cccn3)cc1)C(=O)N([C@H]1CCCC[C@@H]1O)C2]

Step 1: Methyl 2-hydroxy-6-methylnicotinate

To a solution of 2-hydroxy-6-methylnicotinic acid (10.0 g, 0.0653 mole) in methanol (100 mL), sulfuric acid (3.5 mL) was added drop wise at 0° C. and the mixture was stirred for 21 h under reflux. The reaction mixture was concentrated under reduced pressure, the residue was neutralized with saturated aqueous sodium bicarbonate solution under ice-cooling, and the mixture was extracted with 5% methanol in chloroform (200 mL×3). Organic layer was washed with brine solution (50 mL) and dried over $Na_2SO_4$ and the solvent was concentrated under vacuum to afford the title compound.

Yield: 7.0 g, 64.1%; $^1$H-NMR (DMSO-$d_6$, 400 MHz) δ ppm: 2.23 (s, 3H), 3.70 (s, 3H), 6.09-6.11 (d, J=7.24 Hz, 1H), 7.98-8.00 (d, J=7.36 Hz, 1H), 12.10 (s, 1H); Mass (m/z): 168.1 (M+H)$^+$.

Step 2: Methyl 5-bromo-2-hydroxy-6-methylnicotinate

To a solution of methyl 2-hydroxy-6-methylnicotinate (7.0 g, 0.0419 mole) in acetic acid (100 mL), bromine (3.30 mL, 0.062 mole) was added drop wise at room temperature and the mixture was stirred for 3 h. The reaction mixture was concentrated under reduced pressure; the residue was neutralized with ammonia solution under ice-cooling, pH 8, and extracted with 5% methanol in chloroform (300 mL×3). Organic layer was washed with brine solution (50 mL) and dried over $Na_2SO_4$ and the solvent was concentrated under vacuum to afford the title compound.

Yield: 10.0 g, 96.99%; $^1$H-NMR (DMSO-$d_6$, 400 MHz) δ ppm: 2.33 (s, 3H), 3.73 (s, 3H), 8.08 (s, 1H), 12.30 (s, 1H); Mass (m/z): 246 (M+H)$^+$, 248 (M+H)$^+$.

Step 3: Methyl 5-bromo-6-methyl-2-trifluoromethanesulfonyloxynicotinate

To a solution of methyl 5-bromo-2-hydroxy-6-methylnicotinate (6.0 g, 0.0243 mole) in DMF (100 mL), sodium hydride (1.74 g, 0.0365 mole) and N-phenylbis(trifluoromethane sulfonamide) (9.58 g, 0.0268 mole) were added under ice-cooling and the mixture was stirred at room temperature for 17 h. Reaction mixture was diluted with 300 mL ethyl acetate and filtered through celite. The filtrate was washed with 300 mL water and saturated brine 90 mL, dried over $Na_2SO_4$ and the solvent was concentrated under vacuum to afford the crude compound. This was purified by silica gel column chromatography (5% ethyl acetate/hexane) to give the title compound.

Yield: 4.60 g, 50.0%; $^1$H-NMR (DMSO-$d_6$, 400 MHz) δ ppm: 2.64 (s, 3H), 3.90 (s, 3H), 8.67 (s, 1H); Mass (m/z): 378 (M+H)$^+$, 380 (M+H)$^+$.

Step 4: Methyl 5-bromo-6-methyl-2-vinylnicotinate

To a solution of methyl 5-bromo-6-methyl-2-trifluoromethanesulfonyloxynicotinate (3.0 g, 0.00793 mole) in DMF (20 mL), were added tributylvinyltin (2.31 mL, 0.00793 mole), dichlorobis (triphenylphosphine) palladium (0.278 g, 0.000396 mole) and lithium chloride (2.66 g, 0.0634 mole), and the mixture was stirred at 90° C. for 2 h under nitrogen atmosphere. To the reaction mixture was added aqueous potassium fluoride solution, and filtered through celite. The filtrate was diluted with 300 mL ethyl acetate, and the mixture was washed with water and saturated brine 90 mL. The organic layer was dried over anhydrous $Na_2SO_4$ and the solvent was concentrated under vacuum to afford crude compound. The residue was purified by silica gel column chromatography (4% ethyl acetate/hexane) to give the title compound.

Yield: 1.58 g, 79%; $^1$H-NMR (DMSO-$d_6$, 400 MHz) δ ppm: 2.64 (s, 3H), 3.85 (s, 3H), 5.59-5.62 (dd, J=2.11 Hz, 10.57 Hz, 1H), 6.43-6.48 (dd, J=2.02 Hz, 16.89 Hz, 1H), 7.41-7.48 (dd, J=11.66 Hz, 17.90 Hz, 1H), 8.31 (s, 1H); Mass (m/z): 256.1 (M+H)$^+$, 258 (M+H)$^+$.

Step 5: Methyl 5-bromo-2-formyl-6-methylnicotinate

To a solution of methyl 5-bromo-6-methyl-2-vinylnicotinate (1.55 g, 0.00605 mole) in premixed solvent of acetone (20 mL), acetonitrile (20 mL), water (20 mL) were added osmium oxide (0.76 g, 0.00302 mole) and sodium periodate (6.47 g, 0.0302 mole), and the mixture was stirred at room temperature for 3 h. The reaction mixture was filtered through celite and the filtrate was extracted with 120 mL ethyl acetate, and the organic layer was washed with water and saturated brine 30 mL. The organic layer was dried over anhydrous $Na_2SO_4$ and the solvent was concentrated under vacuum to afford the title compound.

Yield: 1.35 g, 86.53%; Mass (m/z): 258 (M+H)$^+$, 260 (M+H)$^+$.

Step 6: 3-Bromo-6-(1S,2S-2-hydroxycyclohexyl)-2-methyl-6,7-dihydropyrrolo[3,4-b]pyridin-5-one To a solution of methyl 5-bromo-2-formyl-6-methylnicotinate (1.35 g, 0.00523 mole), (1S,2S)-2-aminocyclohexanol hydrochloride (0.793 g, 0.00523 mole, CAS No. [13374-30-6]), triethyl amine (2.14 mL, 0.01569 mole) in THF (40 mL) was stirred at room temperature for 3 h, and then sodium triacetoxyborohydride (3.32 g, 0.01569 mole) was added to the reaction mixture and it was stirred at room temperature for 41 h, the reaction mixture was concentrated and added 60 mL ice cold water, neutralized with ammonia and extracted with 120 mL chloroform, and the organic layer was washed with water and saturated brine 30 mL. The organic layer was dried over anhydrous $Na_2SO_4$ and the solvent was concentrated under vacuum to afford crude compound. The residue was purified by silica gel column chromatography (0-2% methanol/dichloromethane) to give the title compound.

Yield: 0.96 g, 56.47%; Mass (m/z): 325 (M+H)$^+$, 327 (M+H)$^+$.

Step 7: 6-(1S,2S-2-Hydroxycyclohexyl)-2-methyl-3-(4,4,5,5-tetramethyl[1,3,2]dioxaborolan-2-yl)-6,7-dihydropyrrolo[3,4-b]pyridin-5-one Dichloro[1,1'-bis(diphenylphosphino)ferrocene]palladium((II) complex with dichloromethane (0.075 g, 0.000092 mole) was added to a stirred mixture of 3-bromo-6-(2-hydroxycyclohexyl)-2-methyl-6,7-dihydropyrrolo[3,4-b]pyridin-5-one (0.3 g, 0.00092 mole), bis(pinacolato)diboron (0.35 g, 0.00138 mole) and potassium acetate (0.54 g, 0.00553 mole) in 1,4-dioxane (20 mL), and the mixture was heated at 110° C. (oil bath temperature) for 3 h. The mixture was cooled to room temperature, diluted with ethyl acetate (30 mL), filtered through celite, washed with brine (10 mL), dried over anhydrous $Na_2SO_4$, filtered and concentrated under vacuum to obtain crude mass of the title compound.

Yield: 0.60 g; Mass (m/z): 373.2 (M+H)$^+$.

Step 8: 6-(1S,2S-2-Hydroxycyclohexyl)-2-methyl-3-(4-pyrazol-1-ylbenzyl)-6,7-dihydropyrrolo[3,4-b]pyridin-5-one Dichloro[1,1'-bis(diphenylphosphino)ferrocene]palladium((II) complex with dichloromethane (0.006 g, 0.0000088 mole) was added to a stirred mixture of 6-(2-hydroxycyclohexyl)-2-methyl-3-(4,4,5,5-tetramethyl[1,3,2]dioxaborolan-2-yl)-6,7-dihydropyrrolo[3,4-b]pyridin-5-one (0.033 g, 0.000088 mole), 1-(4-bromomethyl-phenyl)-1H-pyrazole (0.021 g, 0.000088 mole) and cesium carbonate (0.086 g, 0.000265 mole) in THF (10 mL) and water (1 mL), the mixture was refluxed for 5 h. The mixture was cooled to room temperature, diluted with ethyl acetate (30 mL), washed with brine (10 mL), dried over anhydrous $Na_2SO_4$, filtered and concentrated under vacuum to obtain crude mass of the title compound.

Yield: 0.003 g, 10%; Mass (m/z): 403.1 (M+H)$^+$.

The following example 2 to example 51 were synthesized by following the experimental procedure as described in the preparation of Example 1 using the appropriate intermediate with some non-critical variations.

| Example No. | Structure and IUPAC name | Characterization data |
|---|---|---|
| Example 2 | 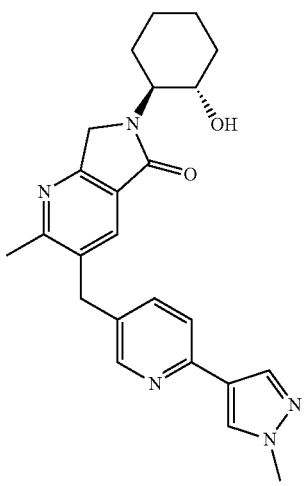<br>6-(1S,2S-2-Hydroxycyclohexyl)-2-methyl-3-[2-(1-methyl-1H-pyrazol-4-yl)pyridin-5-ylmethyl]-6,7-dihydropyrrolo[3,4-b]pyridin-5-one | $^1$H-NMR (DMSO-$d_6$, 400 MHz) δ ppm: 1.23-1.27 (m, 4H), 1.64-1.68 (m, 4H), 2.50 (s, 3H), 3.57 (m, 1H), 3.81 (s, 1H), 3.86 (s, 3H), 4.00 (s, 2H), 4.39 (s, 2H), 4.77-4.78 (d, J = 5.1 Hz, 1H), 7.50-7.58 (m, 2H), 7.79 (s, 1H), 7.94 (s, 1H), 8.23 (s, 1H), 8.40 (s, 1H); Mass (m/z): 418.22 (M + H)$^+$. |
| Example 3 | 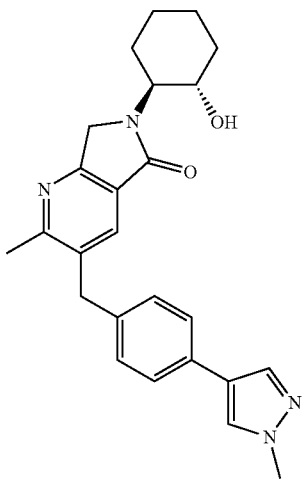<br>6-(1S,2S-2-Hydroxycyclohexyl)-2-methyl-3-[4-(1-methyl-1H-pyrazol-4-yl)benzyl]-6,7-dihydropyrrolo[3,4-b]pyridin-5-one | Mass (m/z): 417.20 (M + H)$^+$. |

| Example No. | Structure and IUPAC name | Characterization data |
|---|---|---|
| Example 4 | 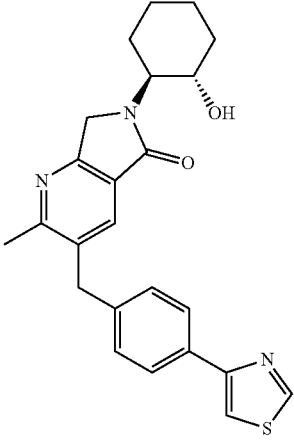<br>6-(1S,2S-2-Hydroxycyclohexyl)-2-methyl-3-(4-thiazol-4-ylbenzyl)-6,7-dihydropyrrolo[3,4-b]pyridin-5-one | $^1$H-NMR (DMSO-$d_6$, 300 MHz) δ ppm: 1.23-1.27 (m, 4H), 1.49-1.67 (m, 4H), 2.50 (s, 3H), 3.56-3.58 (m, 1H), 3.81-3.87 (m, 1H), 4.14 (s, 2H), 4.40 (s, 2H), 4.78-4.80 (d, J = 5.1 Hz, 1H), 7.24-7.26 (d, J = 7.8 Hz, 2H), 7.79 (s, 1H), 7.92-7.94 (d, J = 8.1 Hz, 2H), 8.12 (s, 1H), 9.18 (s, 1H); Mass (m/z): 420.1 (M + H)$^+$. |
| Example 5 | 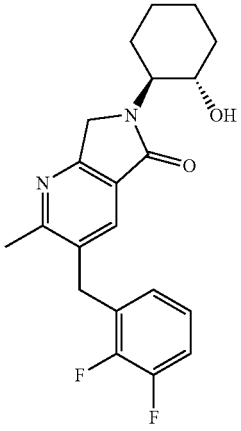<br>6-(1S,2S-2-Hydroxycyclohexyl)-2-methyl-3-(2,3-difluorobenzyl)-6,7-dihydropyrrolo[3,4-b]pyridin-5-one | $^1$H-NMR (DMSO-$d_6$, 400 MHz) δ ppm: 1.25-1.27 (m, 4H), 1.53-1.67 (m, 4H), 2.50 (s, 3H), 3.57 (m, 1H), 3.80-3.86 (m, 1H), 4.17 (s, 2H), 4.40 (s, 2H), 4.71-4.79 (d, J = 4.8 Hz, 1H), 6.95-7.00 (m, 1H), 7.13-7.20 (m, 1H), 7.30-7.39 (m, 1H), 7.67 (s, 1H); Mass (m/z): 373 (M + H)$^+$. |
| Example 6 | 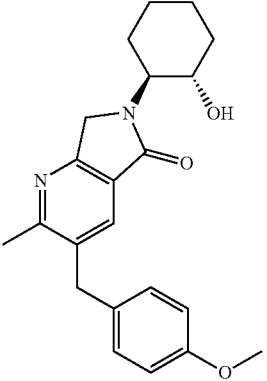<br>6-(1S,2S-2-Hydroxycyclohexyl)-2-methyl-3-(4-methoxybenzyl)-6,7-dihydropyrrolo[3,4-b]pyridin-5-one | $^1$H-NMR (DMSO-d6, 400 MHz) δ ppm: 1.23-1.33 (m, 4H), 1.56-1.67 (m, 4H), 2.50 (s, 3H), 3.56-3.58 (m, 1H), 3.81 (s, 3H), 3.82-3.83 (m, 1H), 4.01 (s, 2H), 4.38 (s, 2H), 4.76-4.77 (d, J = 5.08 Hz, 1H), 6.86-6.88 (d, J = 8.36 Hz, 2H), 7.08-7.10 (d, J = 8.36 Hz, 2H), 7.68 (s, 1H); Mass (m/z): 367.2 (M + H)$^+$. |

| Example No. | Structure and IUPAC name | Characterization data |
|---|---|---|
| Example 7 | 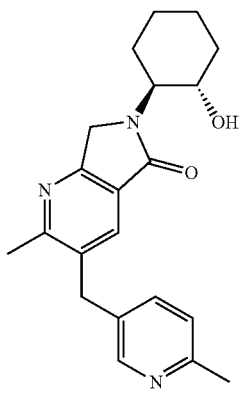<br>6-(1S,2S-2-Hydroxycyclohexyl)-2-methyl-3-(2-methylpyridin-5-ylmethyl)-6,7-dihydropyrrolo[3,4-b]pyridin-5-one | $^1$H-NMR (DMSO-$d_6$, 300 MHz) δ ppm: 1.23-1.27 (m, 4H), 1.52-1.66 (m, 4H), 2.42 (s, 3H), 2.50 (s, 3H), 3.57-3.59 (m, 1H), 3.80-3.88 (m, 1H), 4.07 (s, 2H), 4.39 (s, 2H), 4.77-4.79 (d, J = 5.1 Hz, 1H), 7.16-7.19 (d, J = 8.1 Hz, 1H), 7.41-7.44 (dd, J = 1.8 Hz, 7.8 Hz, 1H), 7.75 (s, 1H), 8.43 (s, 1H); Mass (m/z): 352.2 (M + H)$^+$. |
| Example 8 | 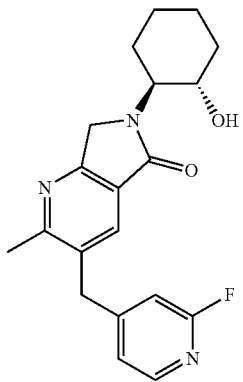<br>6-(1S,2S-2-Hydroxycyclohexyl)-2-methyl-3-(2-fluoropyridin-4-ylmethyl)-6,7-dihydropyrrolo[3,4-b]pyridin-5-one | $^1$H-NMR (DMSO-$d_6$, 300 MHz) δ ppm: 1.23-1.28 (m, 4H), 1.64-1.68 (m, 4H), 2.50 (s, 3H), 3.55-3.57 (m, 1H), 3.84-3.86 (m, 1H), 4.21 (s, 2H), 4.41 (s, 2H), 4.78-4.80 (d, J = 4.5 Hz, 1H), 7.00 (s, 1H), 7.12-7.15 (m, 1H), 7.90 (s, 1H), 8.14-8.15 (m, 1H); Mass (m/z): 356.2 (M + H)$^+$. |
| Example 9 | 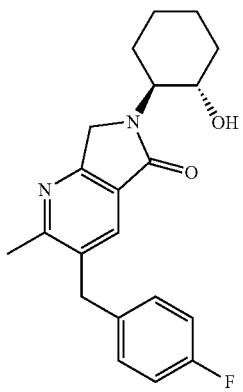<br>6-(1S,2S-2-Hydroxycyclohexyl)-2-methyl-3-(4-fluorobenzyl)-6,7-dihydropyrrolo[3,4-b]pyridin-5-one | $^1$H-NMR (DMSO-d6, 400 MHz) δ ppm: 1.53-1.56 (m, 1H), 1.64-1.67 (m, 4H), 1.90-2.01 (m, 3H), 2.56 (s, 3H), 3.55-3.59 (m, 1H), 3.81-3.86 (m, 1H), 4.09 (s, 2H), 4.39 (s, 2H), 4.77-4.78 (d, J = 4.98 Hz, 1H), 7.11-7.15 (m, 2H), 7.19-7.22 (m, 2H), 7.75 (s, 1H); Mass (m/z): 355.2 (M + H)$^+$. |

| Example No. | Structure and IUPAC name | Characterization data |
|---|---|---|
| Example 10 | 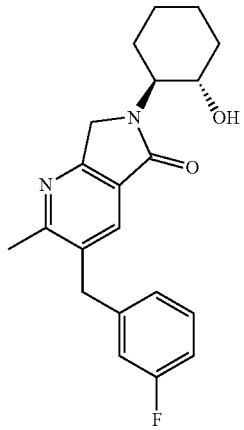<br>6-(1S,2S-2-Hydroxycyclo-hexyl)-2-methyl-3-(3-fluorobenzyl)-6,7-dihydro-pyrrolo[3,4-b]pyridin-5-one | $^1$H-NMR (DMSO-$d_6$, 300 MHz) δ ppm: 1.23-1.30 (m, 4H), 1.53-1.57 (m, 2H), 1.58-1.67 (m, 2H), 2.49 (s, 3H), 3.57-3.59 (m, 1H), 3.81-3.87 (m, 1H), 4.12 (s, 2H), 4.39 (s, 2H), 4.77-4.79 (d, J = 6.8 Hz, 1H), 6.99-7.08 (m, 3H), 7.32-7.39 (m, 1H), 7.78 (s, 1H); Mass (m/z): 355.3 (M + H)$^+$. |
| Example 11 | 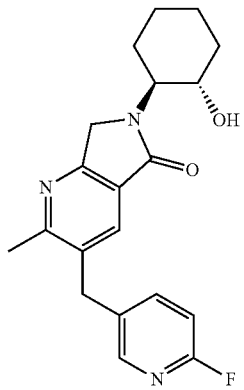<br>6-(1S,2S-2-Hydroxycyclo-hexyl)-2-methyl-3-(2-fluoropyridin-5-ylmethyl)-6,7-dihydropyrrolo[3,4-b]pyridin-5-one | $^1$H-NMR (DMSO-$d_6$, 300 MHz) δ ppm: 1.23-1.27 (m, 4H), 1.53-1.64 (m, 4H), 2.50 (s, 3H), 3.56-3.58 (m, 1H), 3.81-3.84 (m, 1H), 4.13 (s, 2H), 4.39 (s, 2H), 4.77-4.79 (d, J = 5.1 Hz, 1H), 7.10-7.14 (m, 1H), 7.75-7.82 (m, 2H), 8.15 (s, 1H); Mass (m/z): 356.2 (M + H)$^+$. |
| Example 12 | 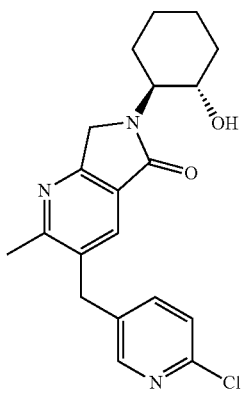<br>6-(1S,2S-2-Hydroxycyclo-hexyl)-2-methyl-3-(2-chloropyridin-5-ylmethyl)-6,7-dihydropyrrolo[3,4-b]pyridin-5-one | $^1$H-NMR (DMSO-$d_6$, 300 MHz) δ ppm: 1.26-1.30 (m, 4H), 1.52-1.68 (m, 4H), 2.50 (s, 3H), 3.56-3.58 (m, 1H), 3.81-3.85 (m, 1H), 4.13 (s, 2H), 4.40 (s, 2H), 4.78 (d, J = 4.8 Hz, 1H), 7.43-7.46 (d, J = 8.1 Hz, 1H), 7.61-7.64 (dd, J = 2.1 Hz, 8.1 Hz, 1H), 7.83 (s, 1H), 8.33 (s, 1H); Mass (m/z): 372.2 (M + H)$^+$. |

-continued

| Example No. | Structure and IUPAC name | Characterization data |
|---|---|---|
| Example 13 | 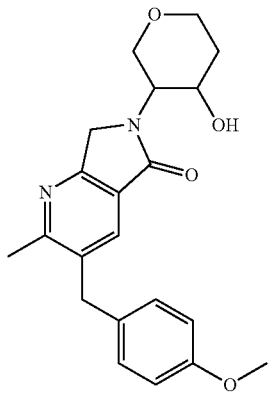<br>6-(4-Hydroxytetrahydropyran-3-yl)-3-(4-methoxybenzyl)-2-methyl-6,7-dihydropyrrolo[3,4-b]pyridin-5-one | $^1$H-NMR (DMSO-$d_6$, 300 MHz) δ ppm: 1.48-1.55 (m, 1H), 1.91-1.95 (m, 1H), 2.50 (s, 3H), 3.01-3.04 (m, 2H), 3.66-3.68 (m, 1H), 3.72 (s, 3H), 3.84-3.87 (m, 3H), 4.02 (s, 2H), 4.44 (s, 2H), 5.10-5.11 (d, J = 3.6 Hz, 1H), 6.86-6.89 (d, J = 8.4 Hz, 2H), 7.07-7.10 (d, J = 8.4 Hz, 2H), 8.32 (s, 1H); Mass (m/z): 369.1 (M + H)$^+$. |
| Example 14 | 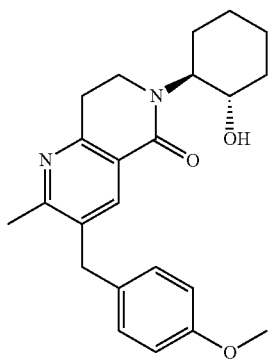<br>6-(1S,2S-2-Hydroxycyclohexyl)-2-methyl-3-(4-methoxybenzyl)-7,8-dihydro-6H-[1,6]naphthyridin-5-one | $^1$H-NMR (DMSO-$d_6$, 300 MHz) δ ppm: 1.23-1.26 (m, 4H), 1.54-1.64 (m, 4H), 2.44 (s, 3H), 2.86-3.07 (m, 2H), 3.48-3.52 (m, 3H), 3.71 (s, 3H), 3.95 (s, 2H), 4.17-4.20 (m, 1H), 4.63-4.65 (d, J = 5.1 Hz, 1H), 6.86-6.88 (d, J = 8.4 Hz, 2H), 7.05-7.08 (d, J = 8.4 Hz, 2H), 7.79 (s, 1H); Mass (m/z): 381.5 (M + H)$^+$. |
| Example 15 | 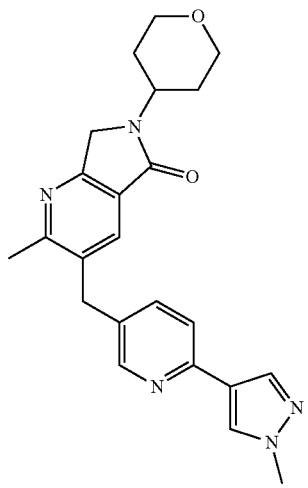<br>6-(Tetrahydropyran-4-yl)-2-methyl-3-[2-(1-methyl-1H-pyrazol-4-yl)pyridin-5-ylmethyl]-6,7-dihydro-pyrrolo[3,4-b]pyridin-5-one | $^1$H-NMR (DMSO-$d_6$, 400 MHz) δ ppm: 1.64-1.67 (m, 2H), 1.80-1.84 (m, 2H), 2.54 (s, 3H), 3.41-3.47 (m, 2H), 3.86 (s, 3H), 3.91-3.95 (m, 2H), 4.09 (s, 2H), 4.27-4.34 (m, 1H), 4.44 (s, 2H), 7.50-7.57 (m, 2H), 7.80 (s, 1H), 7.93 (s, 1H), 8.22 (s, 1H), 8.39 (s, 1H); Mass (m/z): 404.2 (M + H)$^+$. |

-continued

| Example No. | Structure and IUPAC name | Characterization data |
|---|---|---|
| Example 16 | 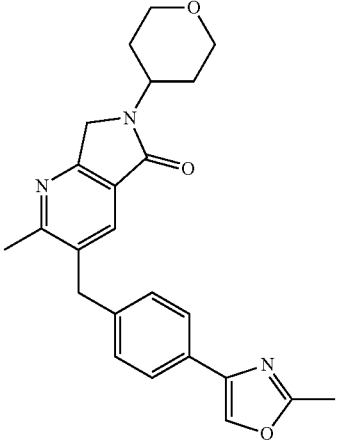<br>6-(Tetrahydropyran-4-yl)-2-methyl-3-[4-(2-methyl-oxazol-4-yl)-benzyl]-6,7-dihydropyrrolo[3,4-b]pyridin-5-one | $^1$H-NMR (DMSO-d$_6$, 400 MHz) δ ppm: 1.64-1.67 (m, 2H), 1.77-1.88 (m, 2H), 2.44 (s, 3H), 2.51 (s, 3H), 3.41-3.47 (m, 2H), 3.92-3.95 (m, 2H), 4.11 (s, 2H), 4.25-4.31 (m, 1H), 4.45 (s, 2H), 7.19-7.21 (d, J = 8.0 Hz, 2H), 7.67-7.69 (d, J = 8.0 Hz, 2H), 7.78 (s, 1H), 8.41 (s, 1H); Mass (m/z): 404.2 (M + H)$^+$. |
| Example 17 | 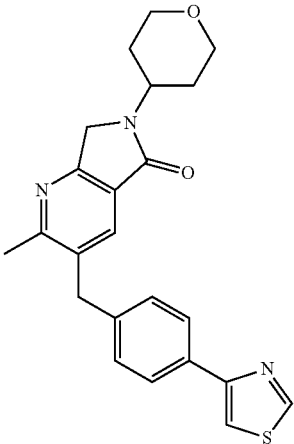<br>6-(Tetrahydropyran-4-yl)-2-methyl-3-(4-thiazol-4-yl-benzyl)-6,7-dihydropyrrolo[3,4-b]pyridin-5-one | $^1$H-NMR (DMSO-d$_6$, 400 MHz) δ ppm: 1.65-1.68 (m, 2H), 1.81-1.85 (m, 2H), 2.53 (s, 3H), 3.42-3.48 (m, 2H), 3.92-3.95 (m, 2H), 4.13 (s, 2H), 4.26-4.28 (m, 1H), 4.45 (s, 2H), 7.23-7.25 (d, J = 8.0 Hz, 2H), 7.79 (s, 1H), 7.92-7.94 (d, J = 8.0 Hz, 2H), 8.11 (s, 1H), 9.17 (s, 1H); Mass (m/z): 406.1 (M + H)$^+$. |
| Example 18 | 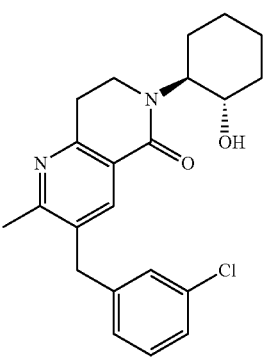<br>6-(1S,2S-2-Hydroxycyclo-hexyl)-2-methyl-3-(3-chlorobenzyl)-7,8-dihydro-6H-[1,6]naphthyridin-5-one | $^1$H-NMR (DMSO-d$_6$, 400 MHz) δ ppm: 1.23-1.29 (m, 4H), 1.48-1.55 (m, 2H), 1.58-1.65 (m, 2H), 2.48 (s, 3H), 2.89-2.93 (m, 1H), 3.01-3.15 (m, 1H), 3.50-3.53 (m, 3H), 4.06 (s, 2H), 4.18-4.20 (m, 1H), 4.61 (s, 1H), 7.10-7.12 (d, J = 7.6 Hz, 1H), 7.23 (s, 1H), 7.27-7.36 (m, 2H), 7.85 (s, 1H); Mass (m/z): 385.2 (M + H)$^+$. |

-continued

| Example No. | Structure and IUPAC name | Characterization data |
|---|---|---|
| Example 19 | 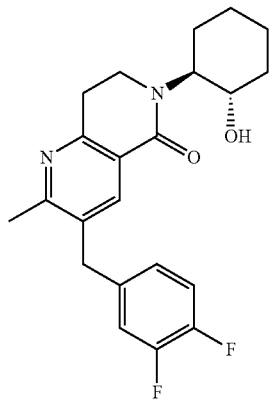<br>6-(1S,2S-2-Hydroxycyclo-hexyl)-2-methyl-3-(3,4-difluorobenzyl)-7,8-dihydro-6H-[1,6]naphthyridin-5-one | $^1$H-NMR (DMSO-$d_6$, 400 MHz) δ ppm: 1.24-1.29 (m, 4H), 1.48-1.51 (m, 2H), 1.60-1.68 (m, 2H), 2.43 (s, 3H), 2.91-2.96 (m, 1H), 3.00-3.07 (m, 1H), 3.49-3.53 (m, 3H), 4.02 (s, 2H), 4.15-4.19 (m, 1H), 4.61-4.62 (d, J = 5.2 Hz, 1H), 6.98 (s, 1H), 7.22-7.27 (t, J = 9.2 Hz, 1H), 7.32-7.39 (d, J = 8.4 Hz, 1H), 7.84 (s, 1H); Mass (m/z): 387.1 (M + H)$^+$. |
| Example 20 | 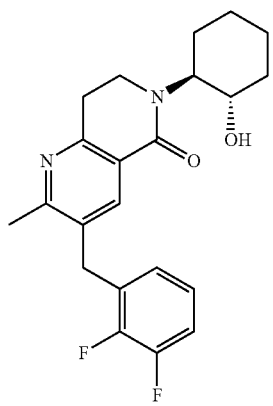<br>6-(1S,2S-2-Hydroxycyclo-hexyl)-2-methyl-3-(2,3-difluorobenzyl)-7,8-dihydro-6H-[1,6] naphthyridin-5-one | $^1$H-NMR (DMSO-$d_6$, 400 MHz) δ ppm: 1.23-1.26 (m, 4H), 1.51-1.54 (m, 2H), 1.62-1.64 (m, 2H), 2.49 (s, 3H), 2.91-3.06 (m, 2H), 3.49-3.52 (m, 3H), 4.10 (s, 2H), 4.15-4.16 (m, 1H), 4.61-4.62 (d, J = 4.8 Hz, 1H), 6.99-7.01 (t, J = 8.8 Hz, 1H), 7.16-7.18 (m, 1H), 7.32-7.35 (m, 1H), 7.76 (s, 1H); Mass (m/z): 387.1 (M + H)$^+$. |
| Example 21 | 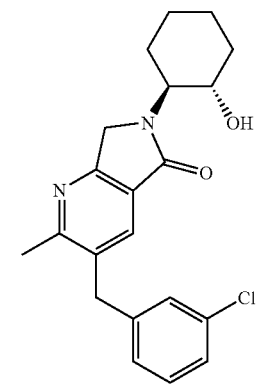<br>6-(1S,2S-2-Hydroxycyclo-hexyl)-2-methyl-3-(3-chlorobenzyl)-6,7-dihydro-pyrrolo[3,4-b]pyridin-5-one | $^1$H-NMR (DMSO-$d_6$, 400 MHz) δ ppm: 1.22-1.28 (m, 4H), 1.53-1.68 (m, 2H), 1.91-1.98 (m, 2H), 2.54 (s, 3H), 3.55-3.60 (m, 1H), 3.81-3.86 (m, 1H), 4.12 (s, 2H), 4.39 (s, 2H), 4.76-4.77 (d, J = 4.0 Hz, 1H), 7.12-7.14 (d, J = 8.0 Hz, 1H), 7.25-7.36 (m, 3H), 7.79 (s, 1H); Mass (m/z): 371.2 (M + H)$^+$. |

| Example No. | Structure and IUPAC name | Characterization data |
|---|---|---|
| Example 22 | 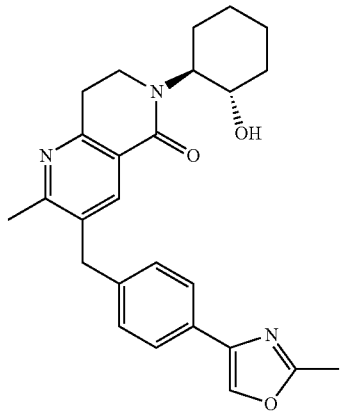<br>6-(1S,2S-2-Hydroxycyclohexyl)-2-methyl-3-[4-(2-methyl-oxazol-4-yl)-benzyl]-7,8-dihydro-6H-[1,6]naphthyridin-5-one | $^1$H-NMR (DMSO-d$_6$, 400 MHz) δ ppm: 1.23-1.29 (m, 4H), 1.48-1.51 (m, 2H), 1.55-1.58 (m, 2H), 2.44 (s, 3H), 2.51 (s, 3H), 2.89-3.01 (m, 2H), 3.49-3.55 (m, 3H), 4.04 (s, 2H), 4.16-4.19 (m, 1H), 4.61-4.63 (d, J = 5.2 Hz, 1H), 7.18-7.20 (d, J = 8.0 Hz, 2H), 7.66-7.68 (d, J = 8.0 Hz, 2H), 7.86 (s, 1H), 8.40 (s, 1H); Mass (m/z): 432.3 (M + H)$^+$. |
| Example 23 | 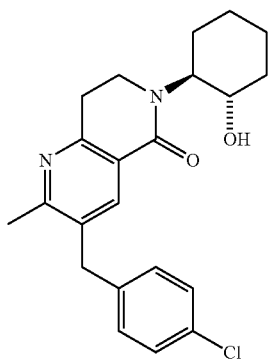<br>6-(1S,2S-2-Hydroxycyclo-hexyl)-2-methyl-3-[4-chlorobenzyl]-7,8-dihydro-6H-[1,6]naphthyridin-5-one | $^1$H-NMR (DMSO-d$_6$, 400 MHz) δ ppm: 1.23-1.30 (m, 4H), 1.49-1.55 (m, 2H), 1.58-1.65 (m, 2H), 2.42 (s, 3H), 2.89-3.07 (m, 2H), 3.49-3.52 (m, 3H), 4.03 (s, 2H), 4.17-4.19 (m, 1H), 4.60-4.61 (d, J = 5.2 Hz, 1H), 7.16-7.18 (d, J = 8.4 Hz, 2H), 7.35-7.37 (d, J = 8.4 Hz, 2H), 7.83 (s, 1H); Mass (m/z): 385.1 (M + H)$^+$. |
| Example 24 | 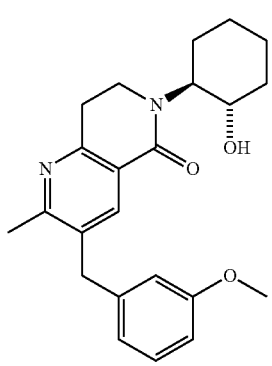<br>6-(1S,2S-2-Hydroxycyclo-hexyl)-2-methyl-3-(3-methoxybenzyl)-7,8-dihydro-6H-[1,6]naph-thyridin-5-one | $^1$H-NMR (DMSO-d$_6$, 300 MHz) δ ppm: 1.23-1.25 (m, 4H), 1.48-1.55 (m, 2H), 1.59-1.66 (m, 2H), 2.54 (s, 3H), 2.89-3.06 (m, 2H), 3.49-3.51 (m, 3H), 3.71 (s, 3H), 3.99 (s, 2H), 4.17-4.19 (m, 1H), 4.63-4.64 (d, J = 4.8 Hz, 1H), 6.68-6.80 (m, 3H), 7.19-7.25 (t, J = 10.4 Hz, 1H), 7.82 (s, 1H); Mass (m/z): 381.1 (M + H)$^+$. |

| Example No. | Structure and IUPAC name | Characterization data |
|---|---|---|
| Example 25 | 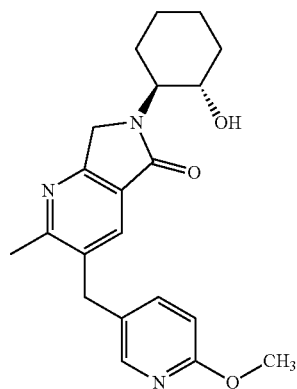<br>6-(1S,2S-2-Hydroxycyclohexyl)-2-methyl-3-(6-methoxypyridin-3-ylmethyl)-6,7-dihydropyrrolo[3,4-b]pyridin-5-one | $^1$H-NMR (DMSO-$d_6$, 400 MHz) δ ppm: 1.23-1.26 (m, 4H), 1.53-1.66 (m, 4H), 2.49 (s, 3H), 3.55-3.57 (m, 1H), 3.81 (s, 3H), 3.82-3.85 (m, 1H), 4.02 (s, 2H), 4.38 (s, 2H), 4.74-4.75 (d, J = 5.2 Hz, 1H), 6.75-6.77 (d, J = 8.4 Hz, 1H), 7.41-7.44 (d, J = 8.1 Hz, 1H), 7.72 (s, 1H), 8.06 (s, 1H); Mass (m/z): 368.2 (M + H)$^+$. |
| Example 26 | 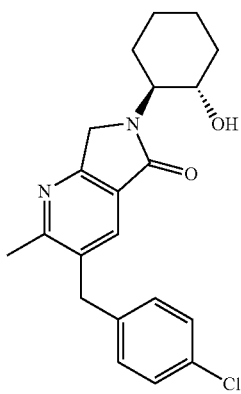<br>6-(1S,2S-2-Hydroxycyclohexyl)-2-methyl-3-(4-chlorobenzyl)-6,7-dihydropyrrolo[3,4-b]pyridin-5-one | $^1$H-NMR (DMSO-$d_6$, 300 MHz) δ ppm: 1.23-1.30 (m, 4H), 1.48-1.55 (m, 2H), 1.58-1.67 (m, 2H), 2.49 (s, 3H), 3.57-3.59 (m, 1H), 3.81-3.87 (m, 1H), 4.10 (s, 2H), 4.39 (s, 2H), 4.77-4.79 (d, J = 4.8 Hz, 1H), 7.18-7.20 (d, J = 8.1 Hz, 2H), 7.35-7.38 (d, J = 8.1 Hz, 2H), 7.78 (s, 1H); Mass (m/z): 371.1 (M + H)$^+$. |
| Example 27 | 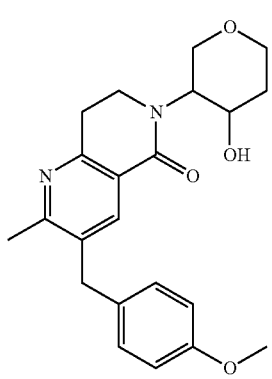<br>6-(4-Hydroxy-tetrahydro-pyran-3-yl)-2-methyl-3-[4-methoxybenzyl]-7,8-dihydro-6H-[1,6]naphthyridin-5-one | $^1$H-NMR (DMSO-$d_6$, 300 MHz) δ ppm: 1.48-1.53 (m, 1H), 1.89-1.93 (m, 1H), 2.44 (s, 3H), 2.90-3.04 (m, 2H), 3.55-3.61 (m, 2H), 3.62-3.66 (m, 2H), 3.72 (s, 3H), 3.79-3.95 (m, 3H), 3.95 (s, 2H), 4.17-4.20 (m, 1H), 4.97-4.98 (d, J = 5.1 Hz, 1H), 6.86-6.89 (d, J = 9.0 Hz, 2H), 7.05-7.08 (d, J = 9.0 Hz, 2H), 7.80 (s, 1H); Mass (m/z): 383.3 (M + H)$^+$. |

| Example No. | Structure and IUPAC name | Characterization data |
|---|---|---|
| Example 28 | 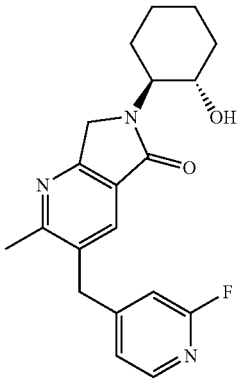<br>6-(1S,2S-2-Hydroxycyclo-hexyl)-2-methyl-3-(2-fluoropyridin-4-ylmethyl)-6,7-dihydropyrrolo[3,4-b]pyridin-5-one | $^1$H-NMR (DMSO-d$_6$, 300 MHz) δ ppm: 1.23-1.28 (m, 4H), 1.49-1.55 (m, 2H), 1.64-1.68 (m, 2H), 2.49 (s, 3H), 3.55-3.57 (m, 1H), 3.84-3.86 (m, 1H), 4.21 (s, 2H), 4.41 (s, 2H), 4.78-4.80 (d, J = 4.5 Hz, 1H), 7.0 (s, 1H) 7.12-7.15 (m, 1H), 7.90 (s, 1H), 8.14-8.15 (m, 1H); Mass (m/z): 356.2 (M + H)$^+$. |
| Example 29 | 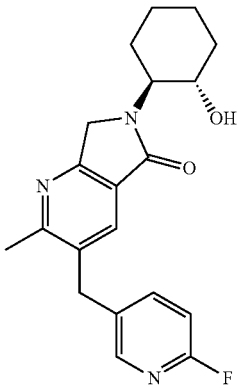<br>6-(1S,2S-2-Hydroxycyclo-hexyl)-2-methyl-3-(6-fluoropyridin-3-ylmethyl)-6,7-dihydropyrrolo[3,4-b]pyridin-5-one | $^1$H-NMR (DMSO-d$_6$, 300 MHz) δ ppm: 1.23-1.27 (m, 4H), 1.53-1.67 (m, 4H), 2.49 (s, 3H), 3.55-3.57 (m, 1H), 3.81-3.85 (m, 1H), 4.13 (s, 2H), 4.39 (s, 2H), 4.77-4.79 (d, J = 5.1 Hz, 1H), 7.10-7.14 (m, 1H) 7.75-7.82 (m, 2H), 8.15 (s, 1H); Mass (m/z): 356.2 (M + H)$^+$. |
| Example 30 | 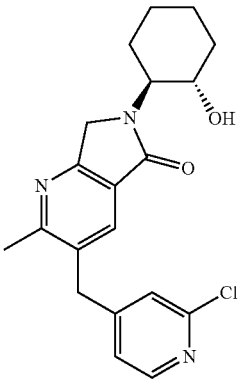<br>6-(1S,2S-2-Hydroxycyclo-hexyl)-2-methyl-3-(2-chloropyridin-4-ylmethyl)-6,7-dihydropyrrolo[3,4-b]pyridin-5-one | $^1$H-NMR (DMSO-d$_6$, 300 MHz) δ ppm: 1.23-1.28 (m, 4H), 1.49-1.55 (m, 2H), 1.64-1.68 (m, 2H), 2.49 (s, 3H), 3.55-3.57 (m, 1H), 3.84-3.86 (m, 1H), 4.21 (s, 2H), 4.41 (s, 2H), 4.78-4.80 (d, J = 4.5 Hz, 1H), 7.0 (s, 1H) 7.12-7.15 (m, 1H), 7.90 (s, 1H), 8.14-8.15 (m, 1H); Mass (m/z): 372.2 (M + H)$^+$. |

| Example No. | Structure and IUPAC name | Characterization data |
|---|---|---|
| Example 31 | 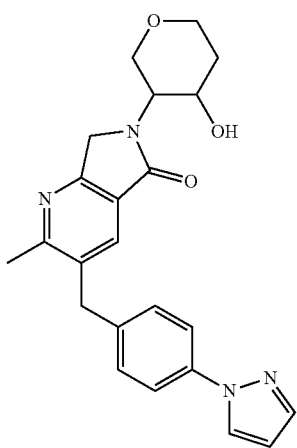<br>6-(4-Hydroxytetrahydropyran-3-yl)-2-methyl-3-(4-pyrazol-1-yl-benzyl)-6,7-dihydro-pyrrolo[3,4-b]pyridin-5-one | $^1$H-NMR (DMSO-$d_6$, 300 MHz) δ ppm: 1.54-1.55 (m, 1H), 1.92-1.95 (m, 1H), 2.52 (s, 3H), 3.32-3.37 (m, 2H), 3.70-3.72 (m, 1H), 3.84-3.89 (m, 3H), 4.14 (s, 2H), 4.46 (s, 2H), 5.09-5.10 (d, J = 3.6 Hz, 1H), 6.52 (s, 1H), 7.27-7.29 (d, J = 8.0 Hz, 2H), 7.71-7.82 (m, 4H), 8.44 (s, 1H); Mass (m/z): 405.5 (M + H)$^+$. |
| Example 32 | 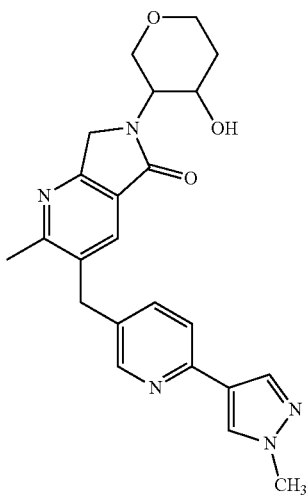<br>6-(4-Hydroxytetrahydropyran-3-yl)-2-methyl-3-[6-(1-methyl-1H-pyrazol-4-yl)-pyridin-3-ylmethyl]-6,7-dihydro-pyrrolo[3,4-b]pyridin-5-one | Mass (m/z): 420.5 (M + H)$^+$. |

| Example No. | Structure and IUPAC name | Characterization data |
|---|---|---|
| Example 33 | 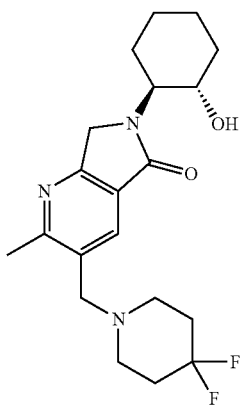<br>6-(1S,2S-2-Hydroxycyclo-hexyl)-2-methyl-3-(4,4-difluoropiperidin-1-ylmethyl)-6,7-dihydropyrrolo[3,4-b]pyridin-5-one | Mass (m/z): 380.1 (M + H)⁺. |
| Example 34 | 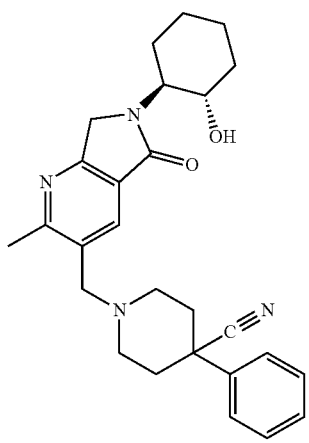<br>1-[6-(1S,2S-2-Hydroxycyclohexyl)-2-methyl-5-oxo-6,7-dihydro-5H-pyrrolo[3,4-b]pyridin-3-ylmethyl]-4-phenyl-piperidine-4-carbonitrile | $^1$H-NMR (DMSO-d$_6$, 300 MHz) δ ppm: 1.23-1.25 (m, 4H), 1.44-1.53 (m, 2H), 1.59-1.66 (m, 2H), 1.98-2.07 (m, 4H), 2.51 (s, 3H), 2.90-3.01 (m, 4H), 3.56-3.59 (m, 1H), 3.67 (s, 2H), 3.82-3.85 (s, 1H), 4.40 (s, 2H), 4.78-4.79 (d, J = 5.1 Hz, 1H), 7.36-7.38 (m, 1H), 7.41-7.46 (m, 2H), 7.51-7.54 (m, 2H), 7.92 (s, 1H); Mass (m/z): 445.1 (M + H)⁺. |
| Example 35 | 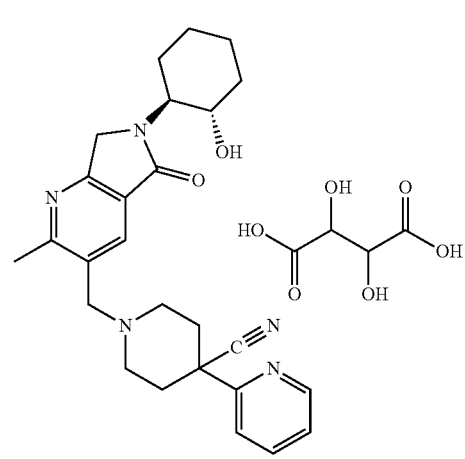<br>1-[6-(1S,2S-2-Hydroxycyclohexyl)-2-methyl-5-oxo-6,7-dihydro-5H-pyrrolo[3,4-b]pyridin-3-ylmethyl]-4-pyridyl-piperidine-4-carbonitrile L-(+)-Tartrate | $^1$H-NMR (DMSO-d$_6$, 300 MHz) δ ppm: 1.23-1.26 (m, 4H), 1.48-1.68 (m, 4H), 2.12-2.14 (m, 4H), 2.51 (s, 3H), 2.62-2.65 (m, 2H), 2.90-2.94 (m, 2H), 3.51-3.62 (m, 1H), 3.67 (s, 2H), 3.82-3.88 (m, 1H), 4.29 (s, 2H), 4.40 (s, 2H), 4.78-4.79 (d, J = 4.8 Hz, 1H), 7.38-7.42 (m, 1H), 7.61-7.64 (d, J = 10.4 Hz, 1H), 7.87-7.92 (m, 2H), 8.61 (s, 1H); Mass (m/z): 446.2 (M + H)⁺. |

| Example No. | Structure and IUPAC name | Characterization data |
|---|---|---|
| Example 36 | 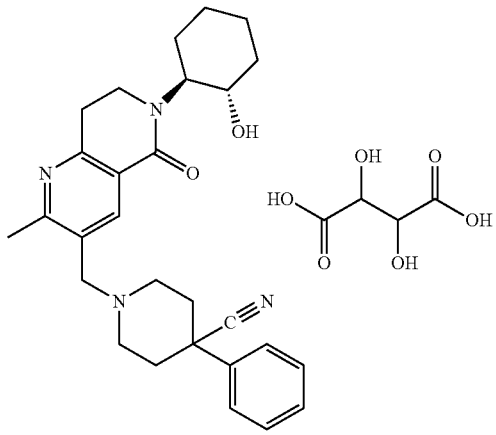<br>1-[6-(1S,2S-2-Hydroxycyclohexyl)-2-methyl-5-oxo-5,6,7,8-tetrahydro-[1,6]naphthyridin-3-ylmethyl]-4-phenyl-piperidine-4-carbonitrile L-(+)-Tartrate | Mass (m/z): 459.1 (M + H)+ |
| Example 37 | 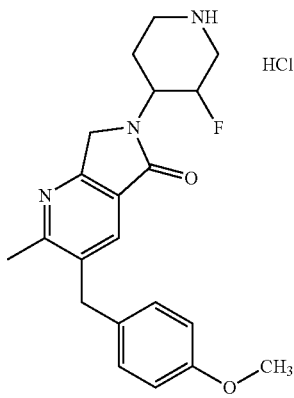<br>6-(3-Fluoro-piperidin-4-yl)-2-methyl-3-(4-methoxybenzyl)-6,7-dihydro-pyrrolo[3,4-b]pyridin-5-one hydrochloride | $^1$H-NMR (DMSO-$d_6$, 300 MHz) δ ppm: 1.23-1.30 (m, 2H), 1.89-1.92 (m, 2H), 2.49 (s, 3H), 3.72 (s, 3H), 4.03 (s, 2H), 4.40 (s, 2H), 4.56-4.62 (m, 2H), 4.71-4.74 (m, 1H), 5.09-5.24 (m, 1H), 6.87-6.89 (d, J = 8.4 Hz, 2H), 7.08-7.10 (d, J = 8.4 Hz, 2H), 7.76 (s, 1H), 8.66-8.68 (bs, 1H), 9.15-9.17 (bs, 1H); Mass (m/z): 370.2 (M + H)+. |
| Example 38 | 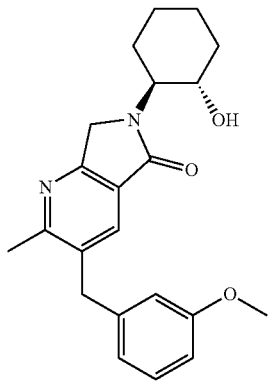<br>6-(1S,2S-2-Hydroxycyclohexyl)-2-methyl-3-(3-methoxybenzyl)-6,7-dihydropyrrolo[3,4-b]pyridin-5-one | $^1$H-NMR (DMSO-$d_6$, 400 MHz) δ ppm: 1.23-1.34 (m, 4H), 1.49-1.67 (m, 4H), 2.52 (s, 3H), 3.54-3.61 (m, 1H), 3.71 (s, 3H), 3.81-3.86 (m, 1H), 4.06 (s, 2H), 4.39 (s, 2H), 4.77-4.78 (d, J = 5.2 Hz, 1H), 6.70-6.72 (d, J = 7.6 Hz, 1H), 6.75 (s, 1H), 6.79-6.81 (dd, J = 2.4, 8.4 Hz, 1H), 7.20-7.24 (d, J = 8.0 Hz, 1H), 7.71 (s, 1H); Mass (m/z): 367.2 (M + H)+. |

| Example No. | Structure and IUPAC name | Characterization data |
|---|---|---|
| Example 39 | 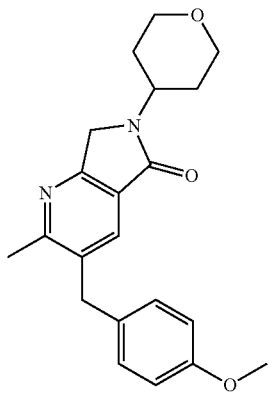<br>6-(Tetrahydro-pyran-4-yl)-2-methyl-3-(4-methoxybenzyl)-6,7-dihydropyrrolo[3,4-b]pyridin-5-one | $^1$H-NMR (DMSO-$d_6$, 400 MHz) δ ppm: 1.64-1.67 (m, 2H), 1.80-1.84 (m, 2H), 2.51 (s, 3H), 3.41-3.46 (m, 2H), 3.72 (s, 3H), 3.91-3.95 (m, 2H), 4.01 (s, 2H), 4.25-4.29 (m, 1H), 4.43 (s, 2H), 6.86-6.88 (d, J = 8.8 Hz, 2H), 7.07-7.09 (d, J = 8.4 Hz, 2H), 7.69 (s, 1H); Mass (m/z): 353.1 (M + H)$^+$. |
| Example 40 | 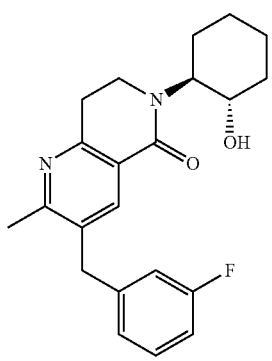<br>6-(1S,2S-2-Hydroxycyclohexyl)-2-methyl-3-(3-fluorobenzyl)-7,8-dihydro-6H-[1,6]naphthyridin-5-one | $^1$H-NMR (DMSO-$d_6$, 400 MHz) δ ppm: 1.23-1.29 (m, 4H), 1.55-1.65 (m, 4H), 2.44 (s, 3H), 2.93-3.03 (m, 2H), 3.50-3.53 (m, 3H), 4.06 (s, 2H), 4.17-4.19 (m, 1H), 4.61-4.62 (d, J = 5.2 Hz, 1H), 6.98-7.07 (m, 3H), 7.32-7.38 (m, 1H), 7.85 (s, 1H); Mass (m/z): 369.1 (M + H)$^+$. |
| Example 41 | 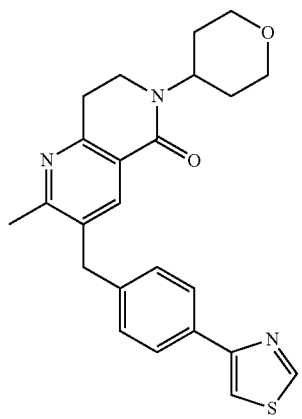<br>6-(Tetrahydro-pyran-4-yl)-2-methyl-3-(4-thiazol-4-yl-benzyl)-7,8-dihydro-6H-[1,6]naphthyridin-5-one | $^1$H-NMR (DMSO-$d_6$, 400 MHz) δ ppm: 1.49-1.52 (m, 2H), 1.76-1.84 (m, 2H), 2.46 (s, 3H), 2.96-3.00 (m, 2H), 3.38-3.42 (m, 2H), 3.50-3.53 (m, 2H), 3.91-3.94 (m, 2H), 4.07 (s, 2H), 4.62-4.64 (m, 1H), 7.22-7.24 (d, J = 8.0 Hz, 2H), 7.90 (s, 1H), 7.92-7.94 (d, J = 8.0 Hz, 2H), 8.11 (s, 1H), 9.17 (s, 1H); Mass (m/z): 420.1 (M + H)$^+$. |

| Example No. | Structure and IUPAC name | Characterization data |
|---|---|---|
| Example 42 | 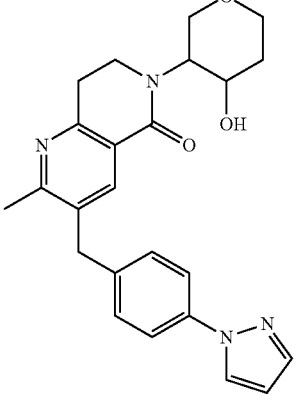<br>6-(4-Hydroxy-tetrahydro-pyran-3-yl)-2-methyl-3-(4-pyrazol-1-yl-benzyl)-7,8-dihydro-6H-[1,6]naphthyridin-5-one | $^1$H-NMR (DMSO-$d_6$, 400 MHz) δ ppm: 1.50-1.53 (m, 1H), 1.90-1.92 (m, 1H), 2.52 (s, 3H), 2.95-3.04 (m, 2H), 3.53-3.66 (m, 4H), 3.80-3.88 (m, 3H), 4.07 (s, 2H), 4.20-4.22 (m, 1H), 4.94-4.95 (d, J = 5.2 Hz, 1H), 6.52 (s, 1H), 7.26-7.28 (d, J = 8.0 Hz, 2H), 7.71 (s, 1H), 7.75-7.77 (d, J = 8.0 Hz, 2H), 7.88 (s, 1H), 8.43 (s, 1H); Mass (m/z): 419.2 (M + H)$^+$. |
| Example 43 | 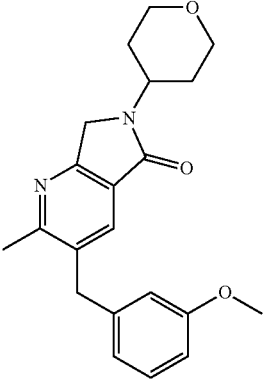<br>6-(Tetrahydro-pyran-4-yl)-2-methyl-3-(3-methoxybenzyl)-6,7-dihydropyrrolo[3,4-b]pyridin-5-one | $^1$H-NMR (DMSO-$d_6$, 400 MHz) δ ppm: 1.65-1.68 (m, 2H), 1.78-1.84 (m, 2H), 2.51 (s, 3H), 3.41-3.47 (m, 2H), 3.71 (s, 3H), 3.91-3.95 (m, 2H), 4.05 (s, 2H), 4.25-4.29 (m, 1H), 4.43 (s, 2H), 6.69-6.71 (d, J = 7.6 Hz, 1H), 6.74 (s, 1H), 6.79-6.81 (dd, J = 2.4, 8.4 Hz, 1H), 7.20-7.24 (t, J = 7.6 Hz, 1H), 7.72 (s, 1H); Mass (m/z): 353.2 (M + H)$^+$. |
| Example 44 | 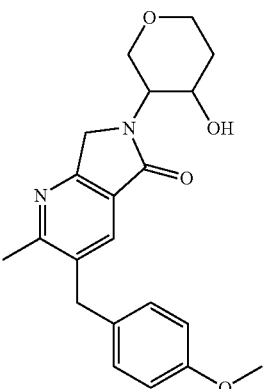<br>6-(4-Hydroxy-tetrahydro-pyran-3-yl)-2-methyl-3-(4-methoxy-benzyl)-6,7-dihydro-pyrrolo[3,4-b]pyridin-5-one-Cis-isomer (Ist Eluting isomer, Peak-I) | $^1$H-NMR (CDCl$_3$, 400 MHz) δ ppm: 1.62-1.66 (m, 1H), 2.36-2.41 (m, 1H), 2.58 (s, 3H), 2.59-2.61 (m, 1H), 3.56-3.62 (m, 1H), 3.67-3.70 (m, 1H), 3.79 (s, 3H), 3.93-3.96 (m, 1H), 3.99 (s, 2H), 4.03-4.13 (m, 2H), 4.45 (s, 2H), 4.84-4.88 (d, J = 18.0 Hz, 1H), 6.82-6.84 (d, J = 8.4 Hz, 2H), 7.01-7.03 (d, J = 8.8 Hz, 2H), 7.78 (s, 1H); Mass (m/z): 369.4 (M + H)$^+$. |

| Example No. | Structure and IUPAC name | Characterization data |
|---|---|---|
| Example 45 | 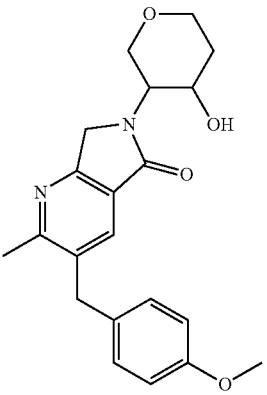<br>6-(4-Hydroxy-tetrahydro-pyran-3-yl)-2-methyl-3-(4-methoxybenzyl)-6,7-dihydro-pyrrolo[3,4-b]pyridin-5-one-Cis, Cis-isomer (IInd Eluting isomer, Peak-II) | $^1$H-NMR (CDCl$_3$, 400 MHz) δ ppm: 1.63-1.66 (m, 1H), 2.35-2.43 (m, 1H), 2.58 (s, 3H), 2.82-2.84 (m, 1H), 3.55-3.62 (m, 1H), 3.67-3.70 (m, 1H), 3.78 (s, 3H), 3.93-3.96 (m, 1H), 3.98 (s, 2H), 4.03-4.13 (m, 2H), 4.45 (s, 2H), 4.84-4.88 (d, J = 18.0 Hz, 1H), 6.82-6.84 (d, J = 8.4 Hz, 2H), 7.00-7.03 (d, J = 8.4 Hz, 2H), 7.77 (s, 1H); Mass (m/z): 369.4 (M + H)$^+$. |
| Example 46 | 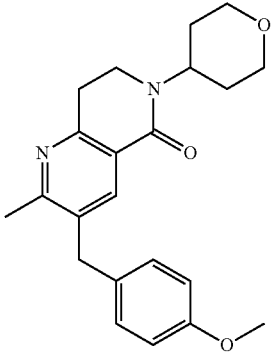<br>6-(Tetrahydro-pyran-4-yl)-2-methyl-3-(4-methoxy-benzyl)-7,8-dihydro-6H-[1,6]naphthyridin-5-one | $^1$H-NMR (DMSO-d$_6$, 400 MHz) δ ppm: 1.48-1.50 (m, 2H), 1.74-1.83 (m, 2H), 2.49 (s, 3H), 2.95-2.98 (m, 2H), 3.40-3.43 (m, 2H), 3.49-3.52 (m, 2H), 3.71 (s, 3H), 3.90-3.91 (m, 2H), 3.95 (s, 2H), 4.59-4.63 (m, 1H), 6.85-6.88 (d, J = 8.4 Hz, 2H), 7.05-7.07 (d, J = 8.4 Hz, 2H), 7.81 (s, 1H); Mass (m/z): 367.1 (M + H)$^+$. |
| Example 47 | 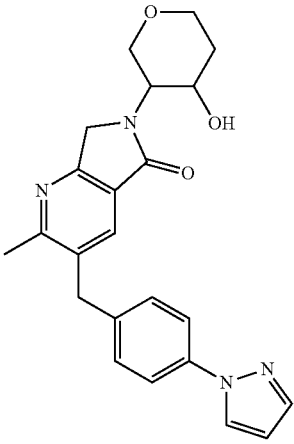<br>6-(Tetrahydro-pyran-4-yl)-2-methyl-3-(4-pyrazol-1-yl-benzyl)-6,7-dihydro-pyrrolo[3,4-b]pyridin-5-one | $^1$H-NMR (DMSO-d$_6$, 400 MHz) δ ppm: 1.64-1.68 (m, 2H), 1.78-1.87 (m, 2H), 2.53 (s, 3H), 3.41-3.47 (m, 2H), 3.92-3.95 (m, 2H), 4.14 (s, 2H), 4.25-4.31 (m, 1H), 4.45 (s, 2H), 6.52 (s, 1H), 7.27-7.29 (d, J = 8.4 Hz, 2H), 7.71 (s, 1H), 7.76-7.78 (d, J = 8.4 Hz, 2H), 7.80 (s, 1H), 8.44-8.45 (d, J = 2.0 Hz, 1H); Mass (m/z): 389.1 (M + H)$^+$. |

| Example No. | Structure and IUPAC name | Characterization data |
|---|---|---|
| Example 48 | 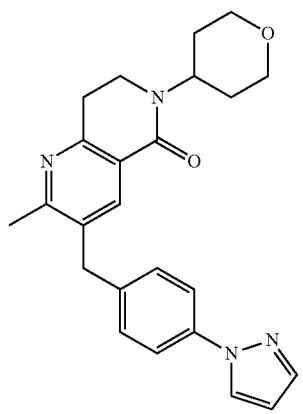<br>6-(Tetrahydro-pyran-4-yl)-2-methyl-3-(4-pyrazol-1-yl-benzyl)-7,8-dihydro-6H-[1,6]naphthyridin-5-one | $^1$H-NMR (DMSO-$d_6$, 400 MHz) δ ppm: 1.48-1.51 (m, 2H), 1.77-1.82 (m, 2H), 2.49 (s, 3H), 2.96-3.01 (m, 2H), 3.44-3.45 (m, 2H), 3.50-3.53 (m, 2H), 3.91-3.94 (m, 2H), 4.07 (s, 2H), 4.59-4.63 (m, 1H), 6.52 (s, 1H), 7.25-7.28 (d, J = 8.4 Hz, 2H), 7.71 (s, 1H), 7.75-7.77 (d, J = 8.4 Hz, 2H), 7.89 (s, 1H), 8.441-8.446 (d, J = 2.0 Hz, 1H); Mass (m/z): 403.4 (M + H)$^+$. |
| Example 49 | 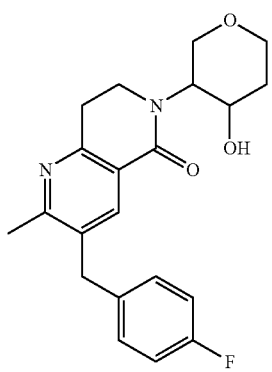<br>6-(4-Hydroxy-tetrahydro-pyran-3-yl)-2-methyl-3-(4-fluorobenzyl)-7,8-dihydro-6H-[1,6]naphthyridin-5-one | $^1$H-NMR (DMSO-$d_6$, 400 MHz) δ ppm: 1.46-1.56 (m, 1H), 1.88-1.93 (m, 1H), 2.44 (s, 3H), 2.92-3.05 (m, 2H), 3.54-3.66 (m, 4H), 3.79-3.90 (m, 3H), 4.02 (s, 2H), 4.19-4.21 (m, 1H), 4.95-4.96 (d, J = 5.2 Hz, 1H), 7.11-7.20 (d, 4H), 7.83 (s, 1H); Mass (m/z): 371.1 (M + H)$^+$. |
| Example 50 | 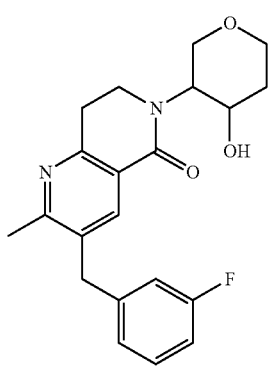<br>6-(4-Hydroxy-tetrahydro-pyran-3-yl)-2-methyl-3-(3-fluorobenzyl)-7,8-dihydro-6H-[1,6]naphthyridin-5-one | $^1$H-NMR (DMSO-$d_6$, 400 MHz) δ ppm: 1.46-1.56 (m, 1H), 1.89-1.93 (m, 1H), 2.44 (s, 3H), 2.94-3.04 (m, 2H), 3.53-3.66 (m, 4H), 3.85-3.89 (m, 2H), 4.06 (s, 2H), 4.08-4.10 (m, 1H), 4.18-4.23 (m, 1H), 4.95-4.96 (d, J = 5.2 Hz, 1H), 6.98-7.07 (d, 3H), 7.32-7.38 (m, 1H), 7.86 (s, 1H); Mass (m/z): 371.1 (M + H)$^+$. |

| Example No. | Structure and IUPAC name | Characterization data |
|---|---|---|
| Example 51 | 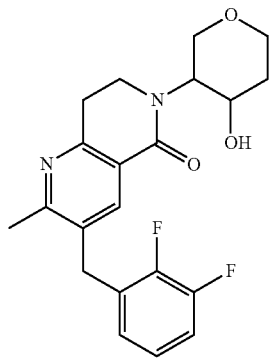<br>6-(4-Hydroxy-tetrahydro-pyran-3-yl)-2-methyl-3-(2,3-difluoro-benzyl)-7,8-dihydro-6H-[1,6]naphthyridin-5-one | $^1$H-NMR (DMSO-$d_6$, 400 MHz) δ ppm: 1.46-1.54 (m, 1H), 1.85-1.91 (m, 1H), 2.49 (s, 3H), 2.95-3.04 (m, 2H), 3.50-3.64 (m, 4H), 3.82-3.87 (m, 3H), 4.10 (s, 2H), 4.18-4.22 (m, 1H), 4.94-4.95 (d, J = 5.2 Hz, 1H), 6.98-7.01 (t, J = 7.2 Hz, 1H), 7.15-7.20 (m, 1H), 7.30-7.37 (m, 1H), 7.77 (s, 1H); Mass (m/z): 389.1 (M + H)$^+$. |

Example 52

Determination of Allosteric Potency $EC_{50}$ Values for Muscarinic M1 Receptor A stable CHO cell line expressing recombinant human Muscarinic M1 receptor and pCRE-Luc reporter system was used for cell-based assay. The assay offers a non-radioactive based approach to determine binding of a compound to GPCRs. In this specific assay, the level of intracellular cyclic AMP which is modulated by activation or inhibition of the receptor is measured. The recombinant cells harbor luciferase reporter gene under the control of cAMP response element.

The above cells were grown in 96 well clear bottom white plates in Hams F12 medium containing 10% fetal bovine serum (FBS). Prior to the addition of compounds or standard agonist, cells were serum starved overnight. Increasing concentrations of test compounds were added along with $EC_{20}$ of acetylcholine in OptiMEM medium to the cells. The incubation was continued at 37° C. in $CO_2$ incubator for 4 h. Medium was removed and cells were washed with phosphate buffered saline. The cells were lysed and luciferase activity was measured in a Luminometer. Luminescence units were plotted against the compound concentrations using Graphpad software. $EC_{50}$ values of the compounds were defined as the concentration required in stimulating the luciferase activity by 50% in presence of $EC_{20}$ of acetylcholine.

| Example No. | $EC_{50}$ (nM) |
|---|---|
| 2 | 288 |
| 4 | 107 |
| 6 | 954 |
| 9 | 1497 |
| 10 | 2781 |
| 13 | 669 |
| 14 | 643 |
| 16 | 1315 |
| 18 | 774 |
| 19 | 972 |
| 24 | 1207 |
| 28 | 929 |
| 38 | 2284 |

Example 53

Rodent Pharmacokinetic Study

Male Wistar rats (260±50 grams) were used as experimental animals. Animals were housed individually in polypropylene cage. Two days prior to study, male Wistar rats were anesthetized with isoflurane for surgical placement of jugular vein catheter. Rats were randomly divided for oral (3 mg/kg) and intravenous (i.v) (1 mg/kg) dosing (n=3/group) and fasted overnight before oral dosing (p.o.). However, rats allocated to intravenous (i.v.) dosing food and water was provided ad libitum.

At pre-determined point, blood was collected through jugular vein and replenished with an equivalent volume of normal saline. Collected blood was transferred into a labeled eppendorf tube containing 10 μL of heparin as an anticoagulant. Typically blood samples were collected at following time points: 0.08, 0.25, 0.5, 1, 2, 4, 6, 8, and 24 h post dose. Blood was centrifuged at 4000 rpm for 10 minutes. Plasma was separated and stored frozen at −80° C. until analysis. The concentrations of the test compounds were quantified in plasma by qualified LC-MS/MS method using suitable extraction technique. The test compounds were quantified in the calibration range around 1-1000 ng/mL in plasma. Study samples were analyzed using calibration samples in the batch and quality control samples spread across the batch.

Pharmacokinetic parameters Cmax, $AUC_t$, $T_{1/2}$, clearance and bioavailability (F) were calculated by non-compartmental model using standard non-compartmental model by using Phoenix WinNonlin 6.0.2 or 6.0.3 version Software package and the results are tabulated below.

| Example No. | ROA | $C_{max}$ (ng/mL) | $AUC_{0-t}$ (ng·hr/mL) | $T_{1/2}$ (hr) | Clearance (mL/min/kg) | F (%) |
|---|---|---|---|---|---|---|
| 6 | oral | 1470 ± 26.5 | 3517 ± 256.6 | 1.3 ± 0.1 | — | 67 ± 5 |
|   | i.v. | — | 1747 ± 312 | 1.9 ± 0.5 | 9.3 ± 2.0 |   |
| 9 | oral | 592 ± 142 | 1290 ± 387 | 1.1 ± 0.4 | — | 35 ± 11 |
|   | i.v. | — | 1223 ± 25 | 1.3 ± 0.3 | 13.5 ± 0.3 |   |
| 38 | oral | 861 ± 168 | 1007 ± 340.3 | 0.6 ± 0.1 | — | 51 ± 17 |
|   | i.v. | — | 662 ± 33 | 0.5 ± 0.0 | 25.1 ± 1.2 |   |

Example 54

Rodent Brain Penetration Study

Male Wistar rats (260±40 grams) were used as experimental animals. Three animals were housed in each cage. Animals were given water and food ad libitum throughout the experiment and maintained on a 12 h light/dark cycle.

Brain penetration was determined in discrete manner in rats. One day prior to dosing day, male Wistar rats were acclimatized and randomly grouped according to their weight. At each time point (0.5, 1 and 2 h) n=3 animals were used.

The test compounds were suitably preformulated and administered orally at (free base equivalent) 3 mg/kg. Blood samples were removed via cardiac puncture by using isoflurane anesthesia. The animals were sacrificed to collect brain tissue. Plasma was separated and brain samples were homogenized and stored frozen at −20° C. until analysis. The concentrations of the test compounds in plasma and brain were determined using LC-MS/MS method.

The test compounds were quantified in plasma and brain homogenate by qualified LC-MS/MS method using suitable extraction technique. The test compounds were quantified in the calibration range of 1-500 ng/mL in plasma and brain homogenate. Study samples were analyzed using calibration samples in the batch and quality control samples spread across the batch. Extent of brain-plasma ratio was calculated ($C_b/C_p$) and the results are tabulated below.

| Example No. | Single dose Rat Brain Penetration ($C_b/C_p$) at 3 mg/kg, p.o. @ 1.0 hr |
|---|---|
| 6 | 0.35 ± 0.08 |
| 9 | 0.25 ± 0.04 |
| 38 | 0.45 ± 0.13 |

Example 55

Protein Binding Assay

Unbound fractions of test compounds in plasma, brain homogenate and liver microsomes were determined using high-throughput dialysis (HT dialysis). Briefly, dialysis membranes were soaked in deionized water for 20 minutes and then in deionized water with 30% ethanol for 15 minutes and finally in phosphate buffer until use. Membranes were rinsed in phosphate buffer before assembling. The membranes were layered between teflon bars of dialysis assembly. Stock solutions of test compound/comparative compound were prepared at 10 mM in DMSO, diluted to 1 mM in acetonitrile and further diluted to 100 μM in mixture of water and acetonitrile (1:1 v/v). Human plasma (pool of 3) was prepared from human blood (3 donors) by centrifuging at 4000 rpm for 10 min at 4° C. Rat and dog blood were obtained on the day of the study and centrifuged to obtain plasma. Rat brains were isolated, cleaned and homogenized with 2 volumes of buffer (3 fold dilution). Liver microsomes were prepared at 0.5 mg/mL in phosphate buffer (100 mM, pH 7.4). The dialysate chambers were loaded with 150 μL of 100 mM phosphate buffer (pH 7.4) in triplicates. The matrix chambers were loaded with 150 μL of the plasma or brain homogenate or microsomal suspension spiked with test compound/comparative compound at a final concentration of 1 μM. 50 μL of the sample was removed from both the chambers at 0 h. The plate was sealed and incubated at 37° C. for 6 h at 100 rpm. After 6 h, 50 μL of the sample was removed from both the chambers. Equal volumes of buffer or human plasma/microsomal suspension were added to the plasma/microsomal and buffer samples respectively to create identical sample matrices for analysis. The samples were precipitated with 150 μL of acetonitrile containing fluoxetine as an internal standard. All the samples were centrifuged at 10000 rpm for 10 minutes at 4° C. The supernatants were analyzed by LC-MS/MS and the results are are tabulated below.

| Example No. | Structure | Species | Fu (Mean ± SEM, n = 3) Plasma | Fu (Mean ± SEM, n = 3) Brain | Fu (Mean ± SEM, n = 3) Microsomes |
|---|---|---|---|---|---|
| Example 6 of instant invention | (structure) | Rat | 0.113 ± 0.003 | 0.123 ± 0.009 | 0.798 ± 0.12 |
|  |  | Dog | 0.115 ± 0.005 | NA | 0.906 ± 0.06 |
|  |  | Human | 0.124 ± 0.003 | NA | 0.938 ± 0.04 |

-continued

| Example No. | Structure | Species | Fu (Mean ± SEM, n = 3) | | |
|---|---|---|---|---|---|
| | | | Plasma | Brain | Microsomes |
| Example 38 of instant invention | 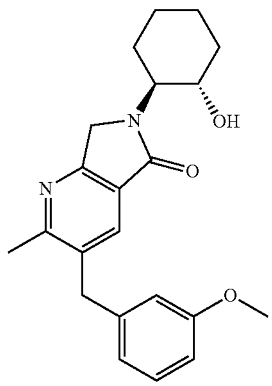 | Rat | 0.103 ± 0.003 | 0.084 ± 0.002 | 0.826 ± 0.03 |
| | | Dog | 0.116 ± 0.007 | NA | 0.843 ± 0.03 |
| | | Human | 0.192 ± 0.003 | NA | 0.870 ± 0.05 |
| Comparative compound (Example no 167 of WO2015163485) | 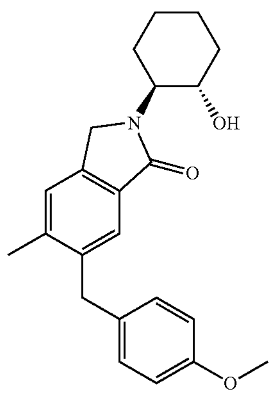 | Rat | 0.0141 ± 0.003 | 0.0022 ± 0.001 | 0.551 ± 0.013 |
| | | Dog | 0.0069 ± 0.004 | NA | 0.709 ± 0.011 |
| | | Human | 0.0063 ± 0.001 | NA | 0.480 ± 0.07 |

Example 56

Object Recognition Task Model

The cognition enhancing properties of compounds of this invention were estimated by using this model.

Male Wistar rats (8-10 weeks old) were used as experimental animals. Four animals were housed in each cage. Animals were kept on 20% food deprivation from a day prior to experimentation. Water was provided ad libitum throughout the experiment. Animals were maintained on a 12 h light/dark cycle in temperature and humidity controlled room. The experiment was carried out in an circular made up of acrylic. Rats were habituated to individual arenas for up to 1 h in the absence of any objects on day 1.

One group of 12 rats received vehicle and another set of animals received compound of the formula (I), before the familiar ($T_1$) and choice ($T_2$) trials. During the familiarization phase, ($T_1$), the rats were placed individually in the arena for 3 minutes, in which two identical objects ($a_1$ and $a_2$) were positioned 10 cm from the wall. 24 h after $T_1$, trial for long-term memory test was performed. The same rats were placed in the same arena as they were placed in $T_1$ trial. During the choice phase ($T_2$) rats were allowed to explore the arena for 3 minutes in presence of a copy of familiar object ($a_3$) and one novel object (b). During the $T_1$ and $T_2$ trial, explorations of each object (defined as sniffing, licking, chewing or having moving vibrissae whilst directing the nose towards the object at a distance of less than 1 cm) were recorded using stopwatch.

$T_1$ is the total time spent exploring the familiar objects ($a_1$+$a_2$).

$T_2$ is the total time spent exploring the familiar object and novel object ($a_3$+b).

The object recognition test was performed as described by Ennaceur, A., Delacour, J., 1988, A new one-trial test for neurobiological studies of memory in rats—Behavioural data, Behav. Brain Res., 31, 47-59.

| Example No. | Dose | Exploration time mean ± S.E.M (sec) | | Inference |
|---|---|---|---|---|
| | | Familiar object | Novel object | |
| 6 | 3 mg/kg, p.o. | 7.27 ± 1.31 | 15.9 ± 2.47 | Active |
| 38 | 3 mg/kg, p.o. | 10.12 ± 2.12 | 19.89 ± 3.32 | Active |

Example 57

Evaluation of Theta Modulation in Dorsal Hippocampus of Anesthetized Male Wistar Rats in Combination with Acetylcholine Esterase Inhibitor Donepezil Effect of M1 PAM compound (Example 38) in combination with donepezil on brain activity as a pharmacodynamic endpoint is evaluated.

Male Wistar rats (240-320 g) were anesthetized by intraperitoneal administration of urethane (1.2 to 1.5 g/kg) for implantation of a catheter in the left femoral vein. The animal was placed in a stereotaxic frame for implanting an electrode (stainless steel wire, Plastics One) into the dorsal hippocampus (AP: 3.8 mm; ML: +2.2 mm; DV: 2.5 mm; Paxinos and Watson, 2004). Bipolar stimulating electrode (untwisted stainless steel wires, separated by 0.75-1.0 mm at their tips, Plastics One) was implanted in the Nucleus Pontis Oralis (NPO; AP: 7.8 mm; ML: 1.8 mm; DV: 6.0 mm; Paxinos and Watson, 2004). Additionally one electrode was implanted into the cerebellum which served as a reference. Hippocampal θ rhythm was evoked via a 6-s electrical stimulation train (20-160 µA, 0.3-ms pulse duration, 250 Hz) delivered to the NPO at a rate of 0.01 trains/s with a Grass S88 stimulator and PSIU6 stimulus isolation unit (Grass Medical Instruments, Quincy, MA). EEG was recorded at a rate of 1000 Hz using Ponemah (Version 5.2) software and stored for off-line analysis using NeuroScore (Version 3.0). Baseline amplitude level was achieved by using the current required to elicit θ rhythm to 50% of the maximal amplitude under control conditions. After the stabilization period of 1 h, baseline recording was done for 30 min followed by the treatment of vehicle or Example 32 (1 mg/kg, i.v.). Donepezil (0.3 mg/kg, i.v.) was administered 30 min after Example 32 treatment and recording was continued for additional 1 h.

Statistical Analysis:

Power in the θ rhythm frequency in the stimulation period during the 30-min baseline period was calculated and the % changes in these measures post treatment were calculated. The percent change in relative theta power after combination of Example 38 and donepezil was compared with donepezil using two-way analysis of variance (time and treatment), followed by Bonferroni's posttest. Statistical significance was considered at a p value less than 0.05.

REFERENCE

1. Paxinos G. and Watson C. (2004) Rat brain in stereotaxic coordinates. Academic Press, New York.

Results

Treatment with donepezil produced moderate increase in hippocampal θ power. Example 38 in combination with donepezil produced significant increase in θ power levels. The effect in combination treatment was observed to be significantly higher than the donepezil alone (FIG. 1).

We claim:

1. A compound selected from the group consisting of:
   6-(1S,2S-2-Hydroxycyclohexyl)-2-methyl-3-(4-thiazol-4-ylbenzyl)-6,7-dihydropyrrolo[3,4-b]pyridin-5-one;
   6-(1S,2S-2-Hydroxycyclohexyl)-2-methyl-3-(4-methoxybenzyl)-6,7-dihydropyrrolo[3,4-b]pyridin-5-one;
   6-(1S,2S-2-Hydroxycyclohexyl)-2-methyl-3-(2-fluoropyridin-4-ylmethyl)-6,7-dihydropyrrolo[3,4-b]pyridin-5-one;
   6-(1S,2S-2-Hydroxycyclohexyl)-2-methyl-3-(4-fluorobenzyl)-6,7-dihydropyrrolo[3,4-b]pyridin-5-one;
   6-(1S,2S-2-Hydroxycyclohexyl)-2-methyl-3-(3-fluorobenzyl)-6,7-dihydropyrrolo[3,4-b]pyridin-5-one;
   6-(1S,2S-2-Hydroxycyclohexyl)-2-methyl-3-(2-fluoropyridin-5-ylmethyl)-6,7-dihydropyrrolo[3,4-b]pyridin-5-one;
   6-(1S,2S-2-Hydroxycyclohexyl)-2-methyl-3-(2-chloropyridin-5-ylmethyl)-6,7-dihydropyrrolo[3,4-b]pyridin-5-one;
   6-(1S,2S-2-Hydroxycyclohexyl)-2-methyl-3-(4-methoxybenzyl)-7,8-dihydro-6H-[1,6]naphthyridin-5-one;
   6-(1S,2S-2-Hydroxycyclohexyl)-2-methyl-3-(3-chlorobenzyl)-7,8-dihydro-6H-[1,6]naphthyridin-5-one;
   6-(1S,2S-2-Hydroxycyclohexyl)-2-methyl-3-(3,4-difluorobenzyl)-7,8-dihydro-6H-[1,6]naphthyridin-5-one;
   6-(1S,2S-2-Hydroxycyclohexyl)-2-methyl-3-(2,3-difluorobenzyl)-7,8-dihydro-6H-[1,6]naphthyridin-5-one;
   6-(1S,2S-2-Hydroxycyclohexyl)-2-methyl-3-(3-chlorobenzyl)-6,7-dihydropyrrolo[3,4-b]pyridin-5-one;
   6-(1S,2S-2-Hydroxycyclohexyl)-2-methyl-3-[4-(2-methyl-oxazol-4-yl)-benzyl]-7,8-dihydro-6H-[1,6]naphthyridin-5-one;
   6-(1S,2S-2-Hydroxycyclohexyl)-2-methyl-3-[4-chlorobenzyl]-7,8-dihydro-6H-[1,6]naphthyridin-5-one;
   6-(1S,2S-2-Hydroxycyclohexyl)-2-methyl-3-(3-methoxybenzyl)-7,8-dihydro-6H-[1,6]naphthyridin-5-one;
   6-(1S,2S-2-Hydroxycyclohexyl)-2-methyl-3-(6-methoxypyridin-3-ylmethyl)-6,7-dihydropyrrolo[3,4-b]pyridin-5-one;
   6-(1S,2S-2-Hydroxycyclohexyl)-2-methyl-3-(4-chlorobenzyl)-6,7-dihydropyrrolo[3,4-b]pyridin-5-one;
   6-(1S,2S-2-Hydroxycyclohexyl)-2-methyl-3-(2-fluoropyridin-4-ylmethyl)-6,7-dihydropyrrolo[3,4-b]pyridin-5-one;
   6-(1S,2S-2-Hydroxycyclohexyl)-2-methyl-3-(6-fluoropyridin-3-ylmethyl)-6,7-dihydropyrrolo[3,4-b]pyridin-5-one;
   6-(1S,2S-2-Hydroxycyclohexyl)-2-methyl-3-(2-chloropyridin-4-ylmethyl)-6,7-dihydropyrrolo[3,4-b]pyridin-5-one;
   6-(1S,2S-2-Hydroxycyclohexyl)-2-methyl-3-(4,4-difluoropiperidin-1-ylmethyl)-6,7-dihydropyrrolo[3,4-b]pyridin-5-one;
   1-[6-(1S,2S-2-Hydroxycyclohexyl)-2-methyl-5-oxo-6,7-dihydro-5H-pyrrolo[3,4-b]pyridin-3-ylmethyl]-4-phenyl-piperidine-4-carbonitrile;
   1-[6-(1S,2S-2-Hydroxycyclohexyl)-2-methyl-5-oxo-6,7-dihydro-5H-pyrrolo[3,4-b]pyridin-3-ylmethyl]-4-pyridyl-piperidine-4-carbonitrile;
   1-[6-(1S,2S-2-Hydroxycyclohexyl)-2-methyl-5-oxo-5,6,7,8-tetrahydro-[1,6]naphthyridin-3-ylmethyl]-4-phenyl-piperidine-4-carbonitrile;
   6-(3-Fluoro-piperidin-4-yl)-2-methyl-3-(4-methoxybenzyl)-6,7-dihydro-pyrrolo[3,4-b]pyridin-5-one;
   6-(1S,2S-2-Hydroxycyclohexyl)-2-methyl-3-(3-methoxybenzyl)-6,7-dihydropyrrolo[3,4-b]pyridin-5-one; and
   6-(1S,2S-2-Hydroxycyclohexyl)-2-methyl-3-(3-fluorobenzyl)-7,8-dihydro-6H-[1,6]naphthyridin-5-one;
   or a pharmaceutically acceptable salt thereof.

2. The compound as claimed in claim 1, wherein the pharmaceutically acceptable salt is selected from the group consisting of:
   1-[6-(1S,2S-2-Hydroxycyclohexyl)-2-methyl-5-oxo-6,7-dihydro-5H-pyrrolo[3,4-b]pyridin-3-ylmethyl]-4-pyridyl-piperidine-4-carbonitrile L-(+)-Tartrate;
   1-[6-(1S,2S-2-Hydroxycyclohexyl)-2-methyl-5-oxo-5,6,7,8-tetrahydro-[1,6]naphthyridin-3-ylmethyl]-4-phenyl-piperidine-4-carbonitrile L-(+)-Tartrate; and
   6-(3-Fluoro-piperidin-4-yl)-2-methyl-3-(4-methoxybenzyl)-6,7-dihydro-pyrrolo[3,4-b]pyridin-5-one hydrochloride.

3. A pharmaceutical composition comprising a compound or a pharmaceutically acceptable salt thereof as claimed in claim 1 and pharmaceutically acceptable excipients, in the treatment of a disease or disorder mediated by muscarinic M1 receptor, wherein said disease or disorder is selected from the group consisting of cognitive disorders, Alzheimer's disease, schizophrenia, pain and sleep disorder.

4. A method of treating a disease or disorder mediated by muscarinic M1 receptor, wherein the disease or disorder is selected from the group consisting of cognitive disorders, Alzheimer's disease, schizophrenia, pain and sleep disorder comprising administering to a patient in need of such treatment, a therapeutically effective amount of a compound or a pharmaceutically acceptable salt thereof as claimed in claim 1.

5. The method of treating a disease or disorder as claimed in claim 4, wherein the cognitive disorder is selected from the group consisting of dementia in Alzheimer's disease, dementia in Parkinson's disease, dementia in Huntington's disease, dementia associated with Down syndrome, dementia associated with Tourette's syndrome, dementia associated with post menopause, frontotemporal dementia, Lewy body dementia, vascular dementia, dementia in HIV, dementia in Creutzfeldt-Jakob disease, substance-induced persisting dementia, dementia in Pick's disease, dementia in schizophrenia and senile dementia.

6. A combination comprising a compound as claimed in claim 1, with one or more therapeutic agents selected from acetylcholinesterase inhibitors and/or NMDA receptor antagonist.

7. The combination as claimed in claim 6, wherein the acetylcholinesterase inhibitor is selected from the group consisting of donepezil, rivastigmine, tacrine and galantamine or a pharmaceutically acceptable salt thereof.

8. The combination as claimed in claim 6, wherein the NMDA receptor antagonist is memantine or a pharmaceutically acceptable salt thereof.

9. A method of treating a disease or disorder mediated by muscarinic M1 receptor selected from cognitive disorders, Alzheimer's disease, schizophrenia, pain or sleep disorder comprising administering to a patient in need of such treatment a therapeutically effective amount of a combination as claimed in claim 6.

* * * * *